US009409880B2

(12) United States Patent
Yin et al.

(10) Patent No.: US 9,409,880 B2
(45) Date of Patent: Aug. 9, 2016

(54) MODULATORS OF TLR3/DSRNA COMPLEX AND USES THEREOF

(75) Inventors: Hang Yin, Boulder, CO (US); Kui Cheng, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 147 days.

(21) Appl. No.: 13/980,874

(22) PCT Filed: Jan. 13, 2012

(86) PCT No.: PCT/US2012/021207
§ 371 (c)(1),
(2), (4) Date: Dec. 18, 2013

(87) PCT Pub. No.: WO2012/099785
PCT Pub. Date: Jul. 26, 2012

(65) Prior Publication Data
US 2014/0094507 A1    Apr. 3, 2014

Related U.S. Application Data

(60) Provisional application No. 61/434,492, filed on Jan. 20, 2011.

(51) Int. Cl.
| | | |
|---|---|---|
| C07D 333/70 | (2006.01) | |
| A61K 31/381 | (2006.01) | |
| A61K 31/404 | (2006.01) | |
| C07C 311/19 | (2006.01) | |

(52) U.S. Cl.
CPC ............ *C07D 333/70* (2013.01); *A61K 31/381* (2013.01); *A61K 31/404* (2013.01); *C07C 311/19* (2013.01)

(58) Field of Classification Search
None
See application file for complete search history.

(56) References Cited

FOREIGN PATENT DOCUMENTS

| BE | WO2007/138112 | * 12/2007 | .......... C07D 333/54 |
|---|---|---|---|
| WO | 01/21584 A1 | 3/2001 | |
| WO | 02/057246 A2 | 7/2002 | |
| WO | 02/057249 A1 | 7/2002 | |
| WO | 02/057270 A1 | 7/2002 | |
| WO | 2004/007501 A1 | 1/2004 | |
| WO | 2011/051671 A1 | 5/2011 | |

OTHER PUBLICATIONS

Ibrahim et al. discloses in Scientist of Physical Sciences (1992), 4(1), 27-33 (CAS STN Accession No. 1992:531542).*
Ibrahim et al. in in Scientist Physical Sciences 4(1), 27-33 (1992).*
Patani et al. in Chemical Reviews 96, 3147-3176 (1996).*
Nguyen et al. In International Journal of Biomedical Science 2006. pp. 85-100.*
Sheng-Hai Huang et al: "Melatonin decreases TLR3-mediated inflammatory factor expression via inhibition of NF-B activation in respiratory syncytial virus-infected RAW264.7 macrophages", Journal of Pineal Research, vol. 45, No. 1, (Aug. 1, 2008), pp. 93-100, XP055118940.
S A M Shedid et al: "Available on line www Synthesis and antibacterial activity of some new amino acid derivatives of 3-chloro-6-methylbenzo[b] thiophene-2-carboxylic acid", Pharm. Res, 2011, XP055119177.
Chemical Abstracts Service, Columbus, Ohio, US; "L-Phenylalanine, N-[(5-fluorobenzo[b]thien-2-yl) carbonyl-, methylester", Feb. 5, 2009, XP002724789, Database accession No. 1101177-51-8.
Chemical Abstracts Service, Columbus, Ohio, US; "L-Phenylalanine, N-[(3-methylbenzo[b]thien-2-yl) carbonyl]-, methyl ester", Oct. 13, 2008, XP002724790, Database accession No. 1060828-30-9.
Ibrahim T M et al: "Synthesis and biological activity of some 3-chlorobenzothiophene-2-carbonylamino acid derivatives", Scientist of Physical Sciences, vol. 4, No. 1, 1992, pp. 27-33, XP009178087.
Nielsen A L et al: "A diversity optimized combinatorial library for the identification of Fc-fragment binding ligands", Biopolymers, vol. 94, No. 2, 2008, pp. 192-205, XP009178086.

* cited by examiner

*Primary Examiner* — Dennis Heyer
(74) *Attorney, Agent, or Firm* — Don D. Cha; Hamilton DeSanctis & Cha, LLP

(57) ABSTRACT

The present invention provides compounds and compositions that can modulate formation of Toll-like receptor 3 (TLR3) and double-stranded RNA (dsRNA) complex, and methods for using the same. In particular, some aspects of the invention provide compounds of the formula:

$$Ar^2 \underset{Z^1}{\overset{X^2}{\diagdown}} (\phantom{X})_n Ar^1 \quad Z^2 = X^3 \qquad I$$

compositions comprising and methods for using the same, where n, $Ar^1$, $Ar^2$, $X^1$, $X^2$, $X^3$, $Z^1$, and $Z^2$ are those defined herein.

13 Claims, 7 Drawing Sheets

MODULATORS OF TLR3/DSRNA COMPLEX AND USES THEREOF

FIELD OF THE INVENTION

The present invention relates to compounds and compositions that can modulate formation of Toll-like receptor 3 (TLR3) and double-stranded RNA (dsRNA) complex, and methods for using the same.

BACKGROUND OF THE INVENTION

Interfering with protein-protein interactions or protein-nucleic acid interactions have been regarded as daunting goals in drug discovery. Major strides have been made the last decade in developing small molecule agents to target protein-protein interactions. However, regulation of protein-RNA interactions lags behind, primarily due to the fact that RNA molecules pose a particular challenge with their high flexibility. RNA-binding proteins (RBPs) play key roles in post-transcriptional modifications, which, along with transcriptional regulation, is believed to be a main method of controlling patterns of gene expression during development.

Toll-like receptors (TLRs) are highly conserved transmembrane proteins that detect pathogen-associated molecular patterns and elicit pathogen-specific immune responses. Thirteen homologous human TLRs have been reported to date. The ligands for these receptors are highly conserved microbial molecules such as lipopolysaccharides (LPS) (recognized by TLR4), lipopeptides (TLR2 in combination with TLR1 or TLR6), flagellin (TLR5), single-stranded RNA (TLR7 and TLR8), double stranded RNA (TLR3), CpG motif-containing DNA (recognized by TLR9), and profilin present on uropathogenic bacteria (TLR11). TLR3 signaling is activated by dsRNA released from necrotic cells during inflammation or viral infection. TLR3 activation induces secretion of type I interferons and pro-inflammatory cytokines, such as the NF-κB-dependent genes, TNF-α, IL-1, and IL-6 and triggers immune cell activation and recruitment that are protective during certain microbial infections. A dominant-negative TLR3 allele has been associated with increased susceptibility to herpes simplex encephalitis, a serious illness with significant risks of morbidity and death, upon primary infection with HSV-1 in childhood. In mice, TLR3 deficiency is associated with decreased survival upon coxsackie virus challenge. In addition, uncontrolled or sustained innate immune response via TLR3 has been shown to contribute to morbidity and mortality in certain viral infection models including West Nile, phlebovirus, vaccinia, and influenza A. TLR3 has also been implicated to be involved with diseases such as atherosclerosis, systemic lupus erythematosus, and rheumatoid arthritis. Thus, modulation of TLR3 pathways offers an attractive method to fight a variety of diseases.

Despite this potential, the discovery of treatment agents has been slow due to the complexity associated with disrupting the protein-RNA contact: immense effort is required to design individual compounds that target specific RNA-binding domains with high binding affinity, selectivity, and also functional activity in cell-based assays. Nevertheless, the information gained with regards to the residues involved in protein-RNA interactions could enable the development of specific agents to disrupt these interactions and thereby limit their signaling capacity.

Therefore, there is a need for compounds that can modulate TLR3. There is also a need for compounds that can modulate TLR3/dsRNA interaction.

SUMMARY OF THE INVENTION

Some aspects of the invention provide compounds of the formula:

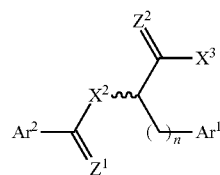

I as well as compositions comprising the same and methods for using the same. In Formula I, n is an integer from 1 to 3, typically n is 1; $Ar^1$ is optionally substituted phenyl, indole, or naphthalene; $Ar^2$ is optionally substituted indolyl (typically indol-2-yl), or naphthalenyl; $X^2$ is —$NR^a$—, —O— or —S—; each of $Z^1$, and $Z^2$ is independently =$NR^a$, =O or =S; $X^3$ is —$NR^aR^b$, —$OR^c$, or —$SR^d$; each $R^a$ is independently hydrogen, alkyl, or a nitrogen protecting group; $R^b$ is hydrogen or alkyl; each $R^c$ is independently hydrogen, alkyl, or a hydroxyl protecting group; $R^d$ is hydrogen, alkyl, or a thiol protecting group. In some embodiments, at least one of $Ar^1$ and $Ar^2$ is substituted.

$Ar^1$ can be substituted with $R_3$, where $R_3$ is alkyl, $OR^c$, halide, $NR^aR^b$, or $SR^d$, and where $R^a$, $R^b$, $R^c$, and $R^d$ are those defined herein.

$Ar^2$ can be substituted with $R^1$, $R^2$, and $R^4$, where each of $R^1$, $R^2$, and $R^4$ is independently alkyl, $OR^c$, halide, $NR^aR^b$, or $SR^d$, and where $R^a$, $R^b$, $R^c$, and $R^d$ are those defined herein.

Typically $R^1$ is halide, alkyl, haloalkyl, —$OR^c$. And $R^2$ is typically halide. Moreover, $R^3$ is typically halide, or —$OR^c$. Furthermore, $R^4$ is typically halide.

In some embodiments, $X^1$ is S.

Still in other embodiments, $Z^1$ and $Z^2$ are O.

Yet in other embodiments, $X^2$ is $NR^a$. Within these embodiments, in some instances $R^a$ is hydrogen.

In other embodiments, $X^3$ is $OR^c$. Within these embodiments, in some instances $R^c$ is hydrogen.

Still yet in other embodiments, $R^1$ is hydrogen, methyl, trifluoromethyl, Cl, F, or methoxy.

In yet other embodiments, $R^2$ is hydrogen, F, or Cl.

Yet in other embodiments, $R^3$ is hydrogen, Cl, or OH.

In other embodiments, $R^4$ is hydrogen or F.

Still in other embodiments, compounds of the invention are of the formula:

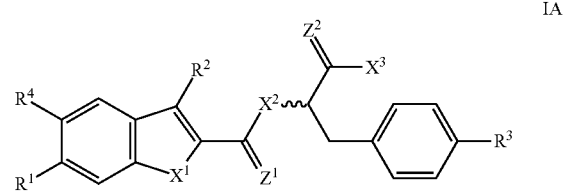

IA where each of $X^1$ and $X^2$ is independently —$NR^a$—, —O— or —S—; each of $Z^1$, and $Z^2$ is independently =$NR^a$, =O or =S; $X^3$ is —$NR^aR^b$, —$OR^c$, or —$SR^d$; each of $R_1$, $R_2$, $R_3$, and $R_4$ is independently hydrogen, alkyl, —$OR^c$, halide, —$NR^aR^b$, or —$SR^d$, provided at least one of $R_1$, $R_2$, $R_3$, and $R_4$ is not hydrogen; each $R^a$ is independently hydrogen, alkyl, or a nitrogen protecting group; $R^b$ is hydrogen or alkyl; each $R^c$ is independently hydrogen, alkyl, or a hydroxyl protecting group; $R^d$ is hydrogen, alkyl, or a thiol protecting group.

In some embodiments, $R_1$ is hydrogen, halide, alkyl, haloalkyl, —$OR^c$; each of $R_2$ and $R_4$ is independently hydrogen or halide; and $R_3$ is hydrogen, halide, or —$OR^c$, and wherein $R^c$ is hydrogen, alkyl, or a hydroxyl protecting group, provided at least one of $R_1$, $R_2$, $R_3$ and $R_4$ is not hydrogen. Within these embodiments, in some instances $R_1$ is hydrogen, methyl, trifluoromethyl, Cl, F, or methoxy. In other instances, $R_2$ is hydrogen, F, or Cl. Yet in other instances, $R_3$ is hydrogen, Cl, or OH. Still in other instances, $R_4$ is hydrogen or F.

Yet other aspects of the invention provides a compound of the formula:

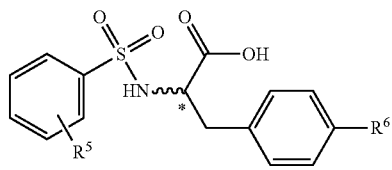

1B where each of $R^5$ and $R^6$ is independently hydrogen, halide, or —$OR^c$, and wherein $R^c$ is hydrogen, alkyl, or a hydroxyl protecting group. In some embodiments, $R^5$ is halide, typically fluoride. Yet in other embodiments, $R^c$ is hydrogen.

Other aspects of the invention provide methods for inhibiting Toll-like receptor 3 (TLR3)/double-stranded RNA (dsRNA) complex formation. Such methods typically comprise contacting a cell with an effective amount of a compound of Formula I.

Still other aspects of the invention provide methods for treating a subject for a clinical condition associated with Toll-like receptor 3 (TLR3)/double-stranded RNA (dsRNA) activation. Such treatment methods typically include administering to the subject a compound of Formula I.

In some embodiments, the clinical condition comprises an infectious disease, an inflammatory disease, or a combination thereof. Within these embodiments, in some instances the clinical condition comprises viral infection, a clinical condition associated with viral infection, atherosclerosis, systemic lupus erythematosus, rheumatoid arthritis, or a combination thereof. While a wide variety virus infection can be treated by methods of the invention, in some particular cases, methods of the invention are used to treat infection of virus, where virus comprises herpes simplex-1, West Nile virus, phlebovirus, vaccinia, influenza A, or a combination thereof.

Yet other aspects of the invention provide methods for treating a clinical condition associated with a Toll-like receptor 3 (TLR3)/double-stranded RNA (dsRNA) interaction in a subject, said method comprising administering to the subject in need of such a treatment a TLR3/dsRNA interaction inhibitor.

In some embodiments, the clinical condition comprises an infectious disease, an inflammatory disease, or a combination thereof. In other embodiments, the clinical condition comprises viral infection, a clinical condition associated with viral infection, atherosclerosis, systemic lupus erythematosus, rheumatoid arthritis, or a combination thereof. In some particular instances, methods of the invention are used to treat infection of virus, where virus comprises herpes simplex-1, West Nile virus, phlebovirus, vaccinia, influenza A, or a combination thereof.

Other aspects of the invention provide compositions comprising a compound disclosed herein.

BRIEF DESCRIPTION OF THE DRAWINGS

FIG. 9 is a graph showing decreasing RANTES production to TLR3 stimulation with increased pre-treatment doses of compound 4a.

DETAILED DESCRIPTION OF THE INVENTION

Figure 1:
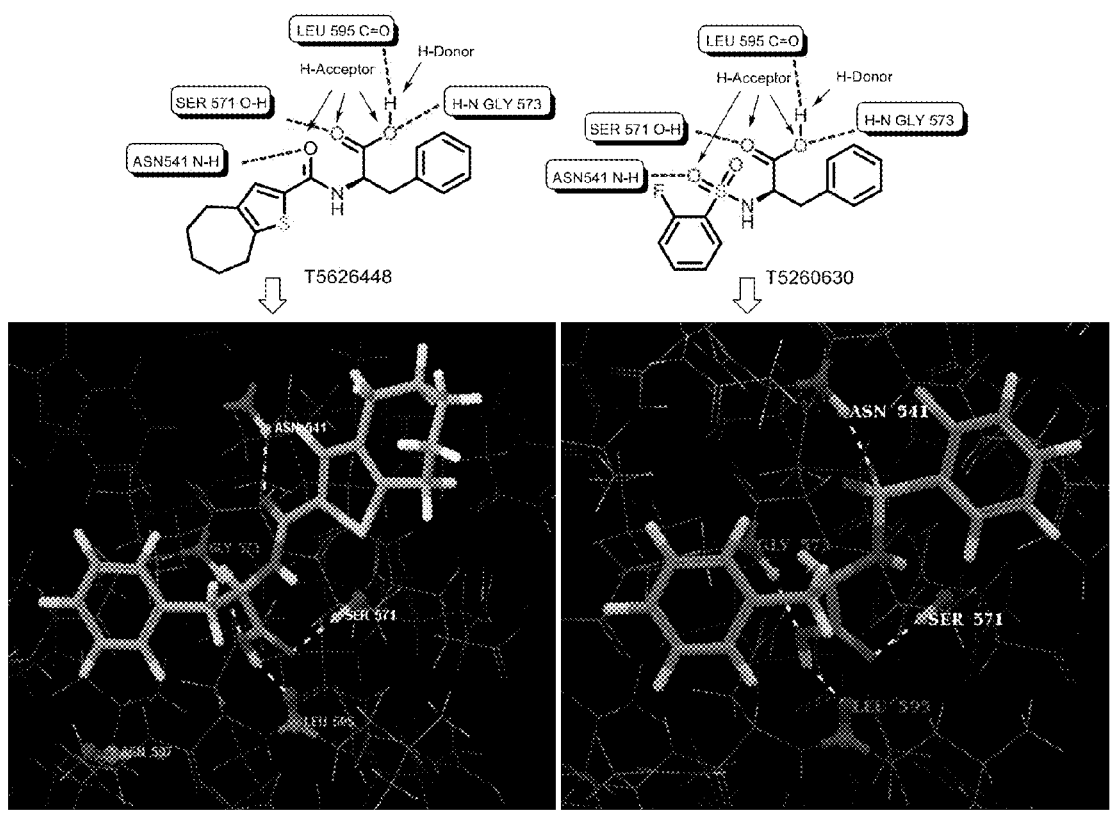
FIG. 1 shows Glide computer simulation model of binding mode of compounds T5626448 and T5260630.

Some aspects of the invention is based on in silico screening and discovery by the present inventors of compounds that can interact with the dsRNA binding region of TLR3. In search of small molecule probes, 1.2 million compounds (from Enamine drug database) were docked into the dsRNA-binding domain of TLR3 (crystal structure PDB: 3CIY) using the program, Glide 5.6. Initial nine hits (FIG. 1) were selected for cell assay screening. Interestingly, all of the hits identified from the in silico screening share the common motif of a D-amino acid with aromatic side chains, implying a novel pharmacophore to target the RNA-binding site of TLR3.

Other aspects of the invention provide compounds that interfere with a dsRNA binding to TLR3 and methods for using the same.

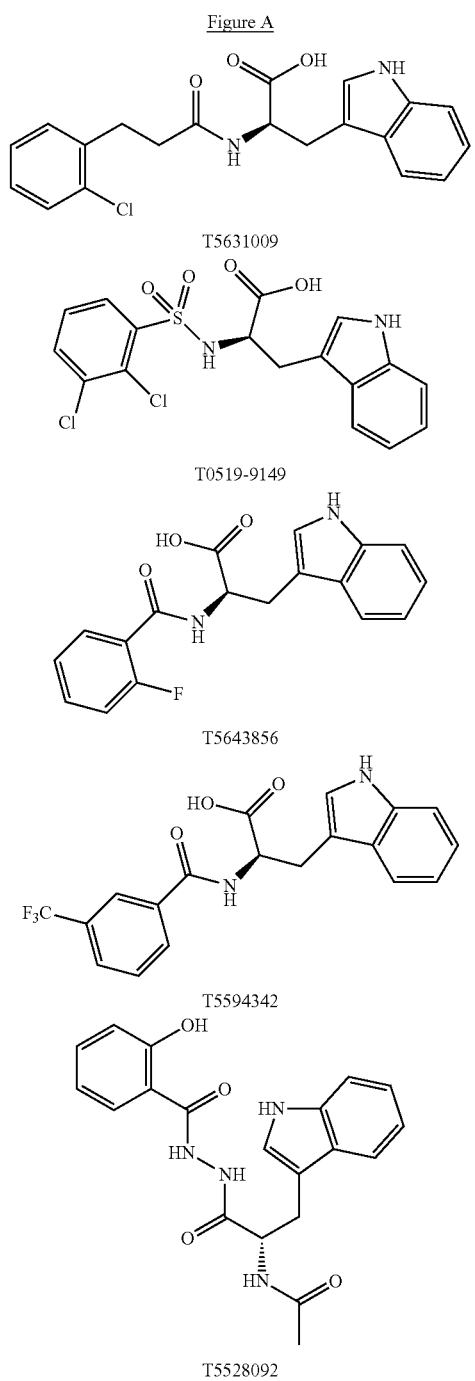

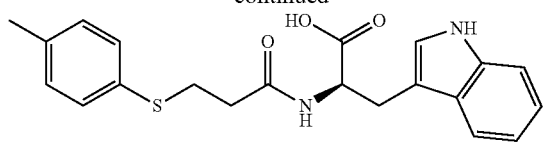

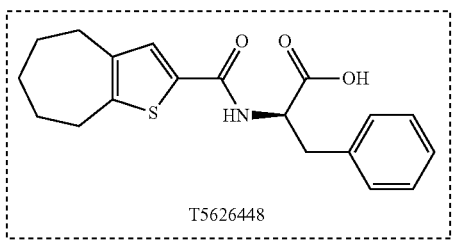

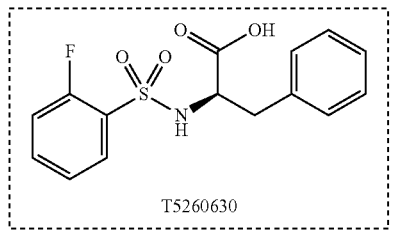

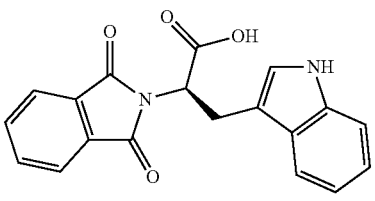

The initial hits (Figure A) were first evaluated using the present inventors' previously established high-throughput cell assay of TLR3 activation. See, for example, *ACS Med. Chem. Lett.* 2010, 1, 194 and *Bioorg. Med. Chem. Lett.*, 2010, 20, 5411. Poly IC (Polyriboinosinic:polyribocytidylic acid) has been reported to selectively activate TLR3 signaling, resulting in the activation of nitric oxide synthase and the production nitric oxide (NO) in RAW 264.7 macrophage cells. The NO level was monitored as an indicator of Poly IC-induced TLR3 activation to evaluate the drug's inhibitory activity.

In cell assay, compounds T5626448 and T5260630 had $IC_{50}$ values of 153.7±5.9 μM and 144.9±3.7 μM, respectively. Both of these compounds are structural derivatives of D-phenylalanine. The homologous motif indicated that the D-phenylalanine scaffold can be used as a core structure to develop small molecule inhibitors of TLR3. The in silico predicted binding modes (FIG. 1) also indicated that the binding affinities of T5626448 and T5260630 can be further modified by varying the substituents on the benzene or thiophene rings.

Scheme 1. Representative Synthetic Scheme
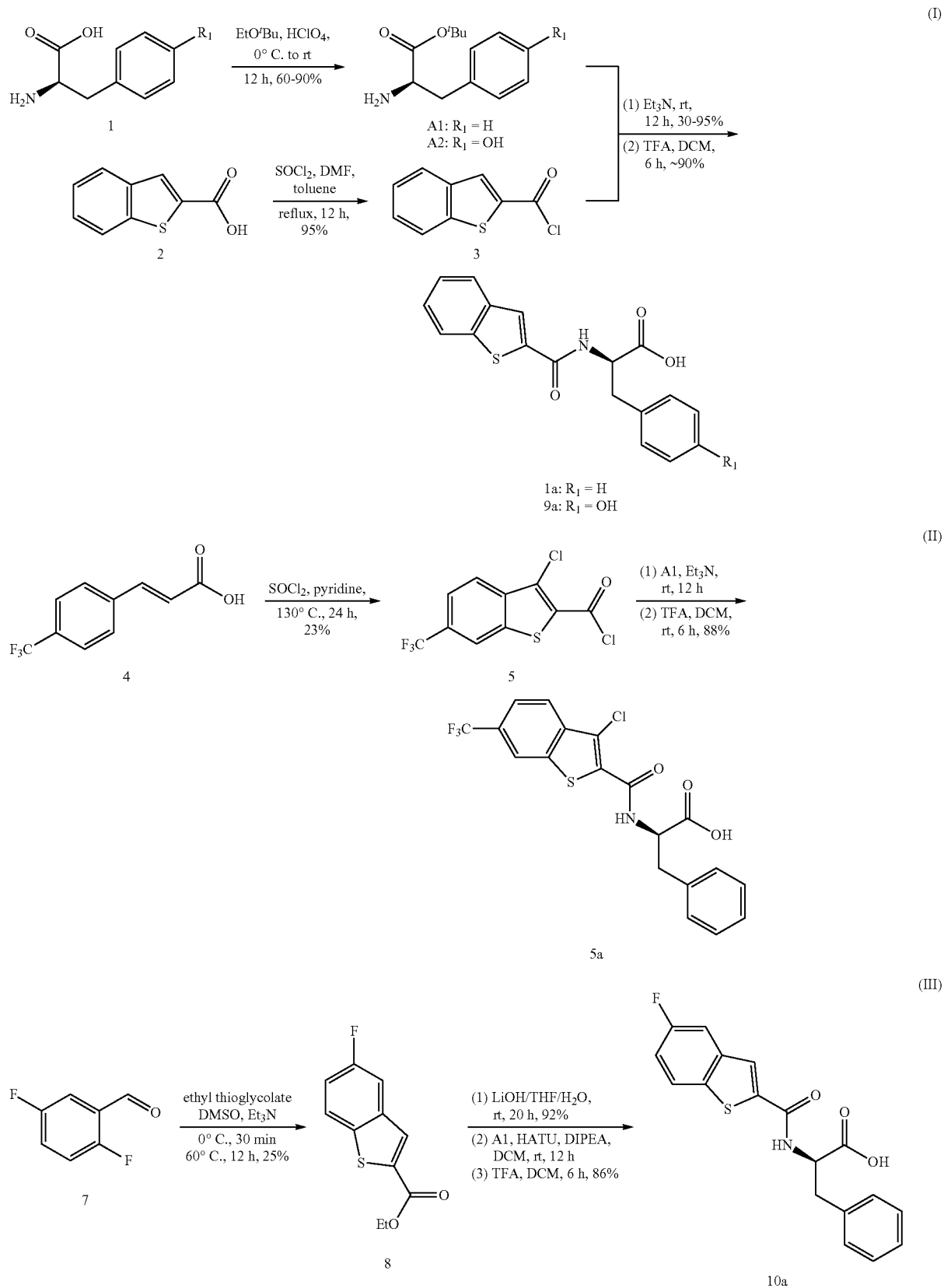

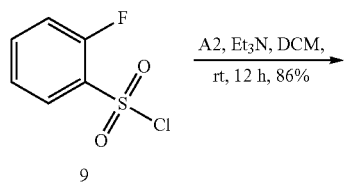

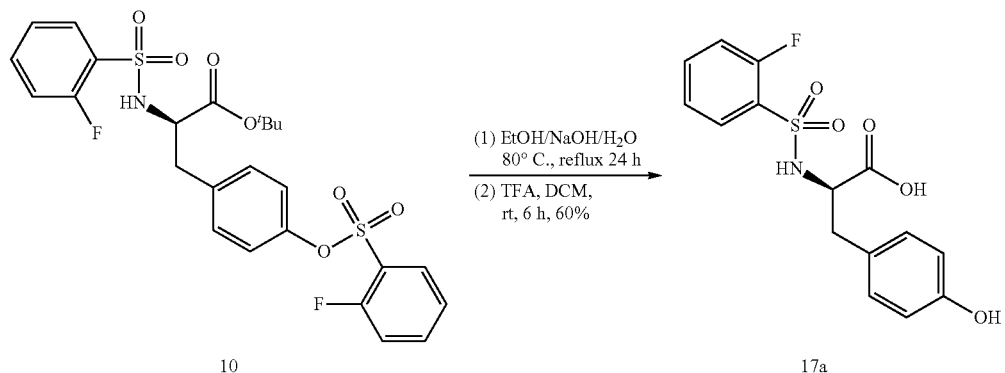

As exemplified in Scheme 1, synthetic routes were developed to allow structure-activity relationship (SAR) analysis. According to isosteric replacement theory, the —F group on the phenyl ring was modified to —Cl or —$CF_3$. To research the electronic effect, the —F group was replaced by —$CH_3$ or —$OCH_3$. Different substitutions on the phenyl group were also examined. To inspect the impact on the activities imposed by the amino acid chiral center, both R- and S-isomers were also incorporated.

An improvement of two orders of magnitude in inhibitory potency of T5626448 was achieved, with compound 4a (see Table 1) that showed a low μM (3.44±0.41 μM) $IC_{50}$ value. Other analogs of T5626448 and T5260630 compounds were synthesized and evaluated for inhibitory activity.

SAR studies of the T5626448 derivatives lent support to the in silico predicted binding mode of this series of TLR3 ligands (Table 1): Substituting a phenyl group for the 7-membered ring position decreased the inhibitory activity (1a and 1b). Without being bound by any theory, one of the reasons may be that the benzene ring is more rigid than the 7-membered ring and does not easily fit into the hydrophobic region. With the replacement by smaller substitutents, —$CH_3$ at the $R_1$ position and —Cl at the $R_2$ position, the activity is increased significantly (5a, 5b). Keeping the chloride at the $R_2$ position, and changing the $R_1$ substituent from —$CH_3$ to —Cl or —F (3a, 4a) resulted in increased activity. The fluoride substituent at $R_1$ position and chloride substituent at $R_2$ position increased the potency significantly by nearly 45-fold (4a) compared to that of T5626448. Again without being bound by any theory, it is believed that this is caused by the sulfur and chloride on the thiophene ring. It is believed that the sulfur on compound 4a is oriented in the opposite direction compared to T5626448, which is believed to have made the chloride more accessible to the hydrophobic curve of His 539.

TABLE 1

Whole cell inhibitory activity assay results.

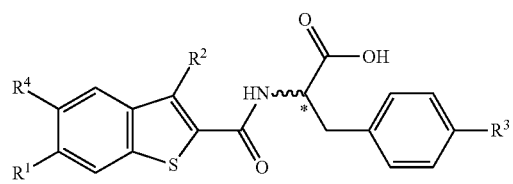

*(R): 1a-13a; (S): 1b-13b

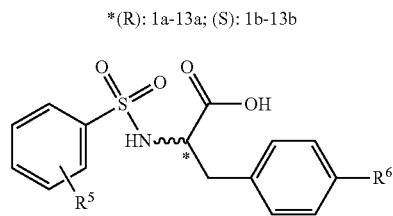

*(R): 14a-19a; (S): 14b-19b

| Compound | $R^1$ | $R^2$ | $R^3$ | $R^4$ | $IC_{50}$ (μM)$^a$ |
|---|---|---|---|---|---|
| T5626448 | | | | | 154 ± 6 |
| T5260630 | | | | | 145 ± 4 |
| 1a | —H | —H | —H | —H | >155 |
| 1b | —H | —H | —H | —H | >155 |
| 2a | —$CH_3$ | —Cl | —H | —H | 11.8 ± 1.3 |
| 2b | —$CH_3$ | —Cl | —H | —H | 31.7 ± 0.7 |
| 3a | —Cl | —Cl | —H | —H | 5.60 ± 0.32 |
| 3b | —Cl | —Cl | —H | —H | 11.8 ± 2.5 |
| 4a | —F | —Cl | —H | —H | 3.44 ± 0.41 |
| 4b | —F | —Cl | —H | —H | 21.9 ± 0.7 |
| 5a | —$CF_3$ | —Cl | —H | —H | 6.28 ± 1.05 |
| 5b | —$CF_3$ | —Cl | —H | —H | 19.8 ± 3.6 |
| 6a | —$OCH_3$ | —Cl | —H | —H | 36.7 ± 3.9 |
| 6b | —$OCH_3$ | —Cl | —H | —H | >100 |
| 7a | —F | —Cl | —OH | —H | 56.4 ± 5.2 |
| 7b | —F | —Cl | —OH | —H | 84.7 ± 2.4 |
| 8a | —F | —F | —Cl | —H | 70.7 ± 2.1 |
| 8b | —F | —F | —Cl | —H | 79.5 ± 3.4 |
| 9a, 9b | —H | —H | —OH | —H | >100 |
| 10a, 10b | —H | —H | —H | —F | >100 |

TABLE 1-continued

Whole cell inhibitory activity assay results.

[Structure: benzothiophene-carboxamide with R¹, R², R⁴ substituents on benzothiophene and R³ on phenyl ring of phenylalanine moiety with COOH]

*(R): 1a-13a; (S): 1b-13b

[Structure: sulfonamide with R⁵ on phenyl sulfonyl and R⁶ on phenylalanine phenyl ring with COOH]

*(R): 14a-19a; (S): 14b-19b

| | | | | | |
|---|---|---|---|---|---|
| 11a, 11b | —H | —Cl | —H | —H | >100 |
| 12a | —H | —H | —Cl | —F | 47.3 ± 4.1 |
| 12b | —H | —H | —Cl | —F | 54.1 ± 5.7 |
| 13a, 13b | —F | —H | —H | —H | >100 |

| | $R^5$ | $R^6$ | $IC_{50}$ (μM) |
|---|---|---|---|
| 14a, 14b | 2-F | —H | >100 |
| 15a, 15b | 3-F | —H | >100 |
| 16a, 16b | 4-F | —H | >100 |
| 17a, 17b | 2-F | —OH | >100 |
| 18a, 18b | 3-F | —OH | >100 |
| 19a, 19b | 4-F | —OH | >100 |

$^a IC_{50}$ average values and corresponding SD values (in μM) were determined from the results of at least three independent tests.

Results showed that in general the greater the electronic withdrawing capability of the group at the $R_1$ position, the more activity was observed. This observation was further supported by compound 6a, where a decrease in the potency by 10-fold (6a vs 4a) with a methoxyl substituent at $R_1$ position was detected. The —$CF_3$ replacement of the —F at $R_1$ position decreased the activity slightly (5a vs 4a). When the fluoride was relocated from the $R_1$ position to $R_4$, the activity decreased significantly (12a vs 4a).

Similarly, multiple adjacent bulky groups for $R_1$, $R_2$-bisubstituents combinations showed a relatively poor inhibition (8a vs 4a and 12a). It is believed that this may be due to the fact that the area near Asn 517 may not be able to physically accommodate bulky substituents. The hydroxyl group at the $R_3$ position also decreased the activity (7a vs 4a). This can be inferred from the predicted docking model: hydrophobic interaction between the benzene ring of phenylalanine and Asn 597 are appreciated. With the absence of any substitute at the $R_1$ and the $R_2$ position, the activity decreased significantly (9a-11a, 13a). When looking at the stereospecificity of all the compounds, the R configurations generally were more potent than the S configurations.

Figure 2:
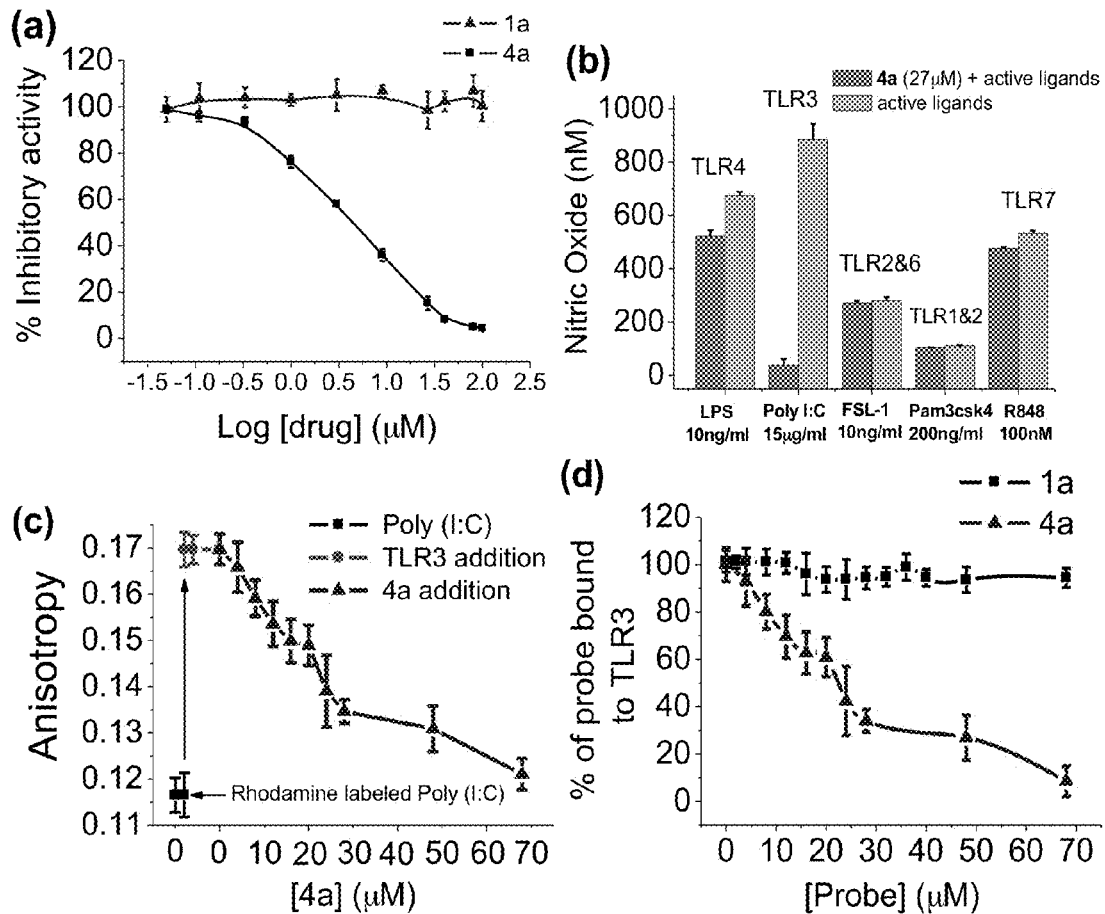
FIG. 2(a) shows dose-dependent inhibitory response graph of Poly IC-induced TLR3 activation by compounds 4a and 1a (negative control).
FIG. 2(b) shows bar graph of specificity test results for compound 4a at 27 μM. LPS, Poly IC, FSL-1, Pam3CSK4 and R848 were used to selectively activate TLR4, TLR3, TLR2/6, TLR2/1 and TLR7 respectively.
FIG. 2(c) is a graph showing competitive binding between compound 4a and dsRNA to TLR3.
FIG. 2(d) is a graph showing the TLR3 binding competition results of compound 4a and 1a with dsRNA. The results show compound 4a competes with dsRNA in binding to TLR3 but the negative control compound 1a does not show any significant binding to TLR3.

The compound 4a demonstrated dose-dependent inhibitory effects blocking Poly IC-induced TLR3 activation with an $IC_{50}$ of 3.44±0.41 μM (FIG. 2a). Compound 4a was tested against a panel of homologous TLRs (i.e., TLR, TLR4, TLR3, TLR2/6, TLR2/1 and TLR7). It was found that compound 4a selectively inhibited TLR3 signaling without significantly affecting other TLRs, showing that it is highly selective in intact cells (FIG. 2b).

Biophysical tests were also carried out for compound 4a along with the negative control compound 1a to demonstrate that 4a directly and specifically binds to TLR3. Fluorescence anisotropy binding showed that 4a competes with dsRNA for binding to TLR3 with a $K_i$ of 2.96±0.32 μM (FIG. 2c). The anisotropy of Rhodamine labeled Poly IC increased from approximately 0.116 to 0.171 upon addition of TLR3 (excitation=546 nm; emission=576 nm). This is consistent with the anisotropy changes seen with ligand-receptor pairs of comparable sizes (Xu, H. Q., Zhang, A. H., Auclair, C., Xi, X. G. Nucleic Acids Res. 2003, 31, e70). Increasing compound 4a's concentration to 68 μM decreased the anisotropy to background levels due to release of the fluorescently labeled Poly IC probe (FIG. 2d). The data is in accord with a one-site-competition model, suggesting that 4a and dsRNA appears to target the same site on the TLR3 surface. Taken together, these results show that 4a is a potent and effective inhibitor of the TLR3/RNA association.

Figure 3:
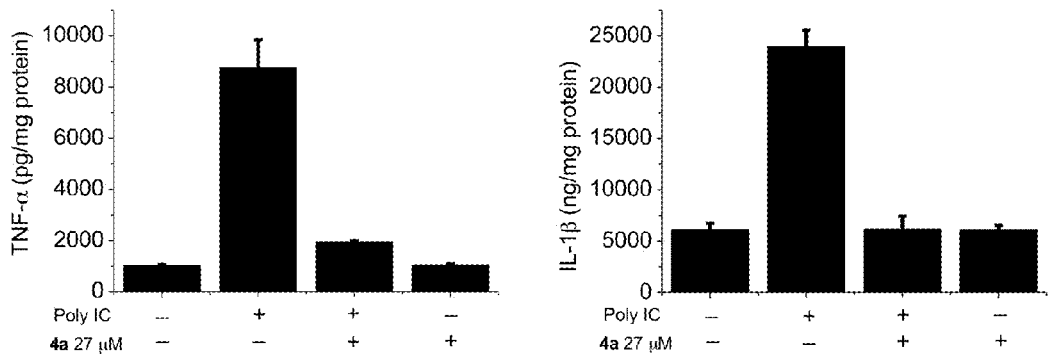
FIG. 3 is a bar graph of ELISA assay results based on the RAW 264.7 cell showing that compound 4a inhibits TNF-α and IL-1β production. The Poly IC dose was 15 μg/mL.

A secondary cell assay was used to confirm that compound 4a inhibits the downstream signaling transduction mediated by the formation of the TLR3/dsRNA complex. In addition to TLR3 signaling suppression, the release of the proinflammatory cytokines, TNF-α and IL-1β, were also studied. These results further confirmed that compound 4a suppresses TLR3-mediated inflammation response (FIG. 3).

Figure 4:
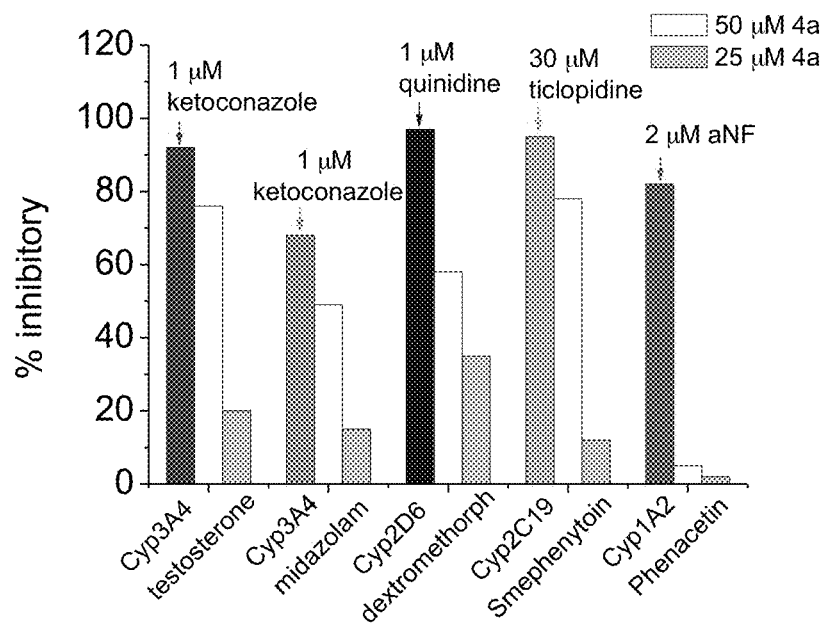
FIG. 4 is a graph of the toxicity test results of compound 4a to different Cytochrome P450 (CYP450) enzymes at 25 μM and 50 μM. Ketoconazole, quinidine, ticlopidine and aNF selectively inhibit Cyp3A4, Cyp2D6, Cyp2C19 and Cyp1A2, respectively.
Figure 5:
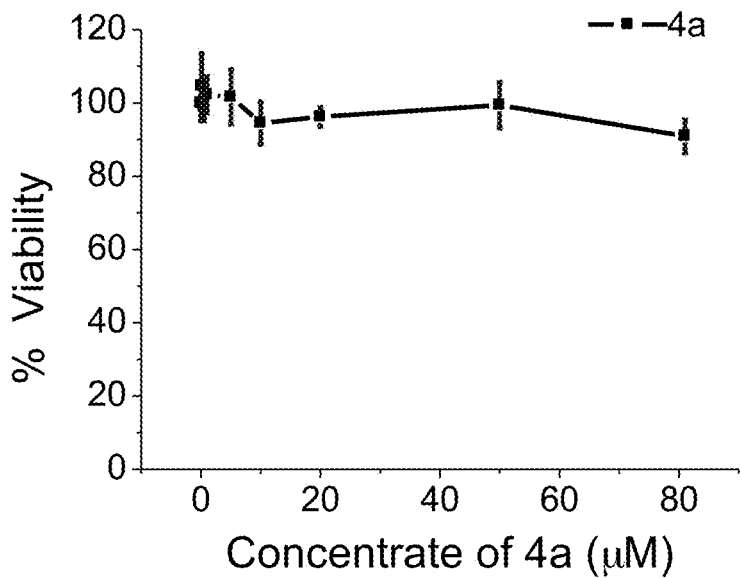
FIG. 5 is a graph showing viability of RAW 264.7 cells in the presence of compound 4a at different concentrations.

Compound 4a was also found to have low toxicity to Cytochrome P450 (CYP450) enzymes, Cyp3A4, 2D6, 2C19 and 1A2, compared to known inhibitors to these specific enzymes (FIG. 4). Furthermore, this compound (FIG. 5) and others did not show any significant toxicity in RAW 264.7 cells as determined by WST-1 methodology.

Compounds of the invention target the dsRNA binding region of TLR3 with good specificity, high binding affinity. Accordingly, compounds of the invention can be used to selectively inhibit TLR3/dsRNA binding.

Synthesis

Compounds of the invention can be made by a variety of methods depicted in the illustrative synthetic reactions described in the Examples section as well as Scheme 1 above. It should be noted that when describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40. It should be appreciated that the synthetic reaction schemes shown in the Examples section and scheme 1 above are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Administration and Pharmaceutical Composition

The present invention includes pharmaceutical compositions comprising at least one compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula (I), as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula (I) or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula (I), or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Utility

Compounds of the invention can be used to treat a wide variety of clinical conditions. As used herein, the term "treat" or "treating" of a clinical condition includes: (1) preventing a clinical condition or a disease, i.e., causing the clinical symptoms of the clinical condition or disease not to develop in a mammal that may be exposed to or predisposed to the clinical condition or disease but does not yet experience or display symptoms of the clinical condition or disease; (2) inhibiting the clinical condition or disease, i.e., arresting or reducing the development of the clinical condition or disease or its clinical symptoms; or (3) relieving the clinical condition or disease, i.e., causing regression of the clinical condition or disease or its clinical symptoms.

Typical clinical conditions related to TLR3 that can be treated by administering a therapeutically effective amount of a compound of the invention include, but not limited to, clinical conditions manifested by (i) an activation of TLR3; (ii) TLR3/dsRNA complex formation; as well as (iii) TLR3/dsRNA activation. As used herein, the term "therapeutically effective amount" means the amount of a compound that, when administered to a mammal for treating a clinical condition or a disease, is sufficient to effect such treatment for the clinical condition or disease. The "therapeutically effective amount" will vary depending on the compound, the clinical condition or the disease and its severity and the age, weight, etc., of the mammal to be treated.

Exemplary clinical conditions that can be treated include, but are not limited to, cancer such as prostate cancer, an infectious disease, an inflammatory disease, viral infection, atherosclerosis, systemic lupus erythematosus, rheumatoid arthritis, or a combination thereof. While a wide variety virus infection can be treated by methods of the invention, in some particular cases, methods of the invention are used to treat infection of virus, where virus comprises herpes simplex-1, West Nile virus, phlebovirus, vaccinia, influenza A, XMRV, or a combination thereof. In addition, compounds of the invention can be used to treat clinical conditions associated with viral infection such as cancer. Exemplary cancers resulting from a viral infection include, but are not limited to, prostate cancer, cervical cancer, etc.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

General Methods

NMR spectra were acquired on Bruker 300 spectrometer, running at 300 MHz for $^1$H and 75 MHz for $^{13}$C, respectively. $^1$H NMR spectra were recorded at 300 MHz in $CDCl_3$ or $(CD_3)_2CO$ using residual $CHCl_3$ (7.28 ppm) and $(CH_3)_2CO$ (2.05 ppm) as the internal standard. $^{13}$C NMR spectra were recorded at 75 MHz in $CDCl_3$ or $(CD_3)_2CO$ using residual $CHCl_3$ (77.16 ppm) and $(CH_3)_2CO$ (29.84 and 206.26 ppm) as internal reference. Thin layer chromatography was performed on Merck Kieselgel 60 Å F254 or Silicycle 60 Å F254 plates eluting with the solvent indicated, visualized by a 254 nm UV lamp, and stained with an ethanolic solution of 12-molybdophosphoric acid. Compounds were purified using flash chromatography (FC) (Silica gel 60, 200-400 mesh, Sorbent Tech.) or recrystallization. Optical rotations (Na D line) were obtained using a microcell with 1 dm path length on a Jasco P-1030 polarimeter. Specific rotations ([α], Unit: ° $cm^2$/g) are based on the equation $\alpha=(100\cdot\alpha)/(l\cdot c)$ and are reported as unit-less numbers where the concentration c is in g/100 mL and the path length l is in decimeters. Mass spectrometry was performed at the mass spectrometry facility of the Department of Chemistry at University of Colorado at Boulder on a double focusing high resolution mass spectrometer. Compounds were named using ChemDraw 11.0. Unless otherwise noted, analytical grade solvents and commercially available reagents were used without further purification.

Virtual Screening

The Enamine drug database (1.2 million small molecules) was docked into the dsRNA and TLR3 binding domain (PDB: 3CIY) using Glide 5.6. The molecules are created, as appropriate, with multiple protonation and tautomeric states. The TLR3 conformations were prepared using standard Glide protocols. This includes addition of hydrogens, restrained energy-minimizations of the protein structure with the Optimized Potentials for Liquid Simulations-All Atom (OPLS-AA) force field, and finally setting up the Glide grids using the Protein and Ligand Preparation Module. All 1.2 million compounds were first docked and ranked using High Throughput Virtual Screening (HTVS) Glide, continued with standard precision (SP) Glide for the top 10000 compounds. The resultant top 5000 compounds were then docked using the more accurate and computationally intensive extra-precision (XP) mode. Initial top-ranked 100 compounds were selected out.

The selection of the candidate molecules was based on the following criteria: (1) Complementarity exists between the ligand and the active site of TLR3. (2) Reasonable chemical structure and pose are in the active site of TLR3. Some unusually highly scored molecules were found to have many rotatable bonds (such as long aliphatic structures), which were excluded for further evaluation. (3) There is formation of at least one hydrogen bond between the ligand and the important residues of TLR3 (such as H is 539, Asn 541, and Ser 571, etc). (4) Protonation state and the tautomeric form of the ligand have to be acceptable. As a result, 100 candidate compounds can meet the above criteria. In order to achieve good chemical diversity, the resulting 100 candidates were subsequently filtered by chemical diversity and binding energy. Consequently, 9 potential TLR3 inhibitors were designated and purchased for vitro assaying.

In Vitro TLR3 Inhibition Assay

RAW 264.7 (Mouse leukaemic monocyte macrophage cell line) cells were grown in RPMI 1640 medium, supplemented with 10% FBS, penicillin (100 U/mL) and streptomycin (100 mg/mL). RAW cells were then planted in 96-well plates at 100,000 cells per well and grown for 24 h in the media descried previously at 37° C. in a 5% $CO_2$ humidified incubator. After 24 h, non-adherent cells and media were removed and replaced with fresh RPMI 1640 medium (only RPMI). The adherent macrophages were treated with high molecular weight polyinosine-polycytidylic acid (Poly IC) (10 μg/mL) (Invivogen), an agonist of TLR3, and then added different concentrates of potential inhibitor. Two rows were only treated with Poly IC as an control. Plates were then incubated for an additional 24 h. Following incubation 100 μL of media was removed and added to flat black 96-well microfluor plates (Thermo Scientific, MA, USA). To each well, 10 μL of 2,3-diaminonaphthalene (0.05 mg/mL in 0.62 M aqueous HCl solution) was added and incubated for 15 min in the dark. The reaction was quenched by addition of 5 μL of a 3 M aqueous NaOH solution and the plate was read on Beckman Coulter DTX880 reader (Beckman Coulter, Calif., USA) with excitation at 365 nm and emission at 450 nm. The nitrite (a stable metabolite of nitric oxide) concentration was determined from a nitrite standard curve. The inhibition rate (%) of NO release was determined using the following formula: Inhibition (%)=[Poly IC($OD_{450}$)−Compounds ($OD_{450}$)]/[Poly IC($OD_{450}$)−Control ($OD_{450}$)]×100. The $IC_{50}$ values for both inhibition and cytotoxicity were determined graphically using software Origin v7.5.

Cytokine-Specific ELISA

RAW cells were planted in 6-well plates at 1,000,000 cells per well with 3 mL of medium (RPMI 1640 medium, supplemented with 10% FBS, penicillin (100 U/mL) and streptomycin (100 mg/mL)) and grown for 24 h at 37° C. in a 5% $CO_2$ humidified incubator. After 24 h, non-adherent cells and media were removed and replaced with fresh RPMI 1640 medium (3 mL/well). Two wells of adherent macrophages were treated with high molecular weight Poly IC (Invivogen, 10 µg/mL), only one well was treated with 27 µM compound 4a. In additionally wells, one well was treated with only 4a (27 µM) and the other was treated with nothing. Plates were then incubated for an additional 24 h. The medium was removed, the cells were washed with PBS (3×1 mL), the 6 well plate was put on ice, then 500 µL of lysis buffer was added in each well (Lysis Buffer: 120 µL 0.5M EDTA; 12 mL Mammalian Protein Extraction Reagent, 100 µL cocktail, 0.36 mL NaCl (5 M, aqueous)). After 5 min, the mixture was transferred into corresponding 1.5 mL tube, spun for 20 min at 13.2 K rpm in a cold room. Approximately 400 µL of supernatant were collected into new tubes, frozen at −80° C. until ready for cytokine measurement. The production of the cytokine interleukin-1β (IL-1β) and TNF-α was quantified with enzyme-linked immunosorbent assays (ELISA) using cytokine-specific capture antibodies, biotinylated monoclonal detection antibodies, and recombinant human cytokine standards according to commercially available ELISA kits from R&D Systems. The cytokine level in each sample was determined in duplicate.

RAW264.7 Cell Nitric Oxide TLR Selectivity Assay

This assay was run in a similar manner as the "In Vitro TLR3 Inhibition Assay". LPS (lipopolysaccharide), FSL-1 ((S,R)-(2,3-bispalmitoyloxypropyl)-Cys-Gly-Asp-Pro-Lys-His-Pro-Lys-Ser-Phe), R848 (4-amino-2-(ethoxymethyl)-α, α-dimethyl-1H-imidazo[4,5-c]quinoline-1-ethanol) and $Pam_3CSK_4$ (N-palmitoyl-S—[2,3-bis(palmitoyloxy)-(2RS)-propyl]-[R]-cysteinyl-[S]-seryl-[S]-lysyl-[S]-lysyl-[S]-lysyl-[S]-lysine.3HCl) were used to selectively activate TLR4, TLR2/6, TLR7 and TLR2/1 in place of Poly IC, respectively.

Fluorescence Anisotropy Assay

In 500 µL Tris buffer (pH=7.2) add 5 µL (1 µg/mL) Rhodamine labeled Poly IC (Invivogen), test the anisotropy at excitation of 546 nm and emission of 576 nm (Horiba Fluorolog 3). An addition 3 µL (20 µM) of TLR3 (R &D) was added in the buffer, then test the anisotropy again. Following, 4a was added in the buffer from 0 to 68 µM, and the fluorescence anisotropy was tested when the concentration was changed.

In Vitro Cytotoxicity Assay

Cytochrome P450 Toxicity Assay

Test agent was incubated (two wells per condition) with microsomes at 37° C. Control incubations containing vehicle or reference inhibitors were run along side the test agents. The final assay contained test agent, probe substrates at the indicated concentration, 2 mM NADPH, 3 mM $MgCl_2$ in 50 mM potassium phosphate buffer, pH 7.4. The final microsomal concentration was 0.5 mg/mL. The maximum solvent concentration in the final assay was ≤0.5% to minimize the inhibition of Cyps by solvent. NADPH was added last to start the assay. At the end of ten minutes incubation, the assay was stopped by the addition of acetonitrile containing internal standard, the samples were centrifuged, and the amount of probe metabolite in the supernatant was determined by LC/MS/MS. (Testing was done by Apredica, Watertown, Mass. using subcellular fractions)

WST-1 Cytotoxicity Assay

This assay was conducted in a 96-well plate with 5,000 cells in 100 µL media (RPMI 1640 medium, supplemented with 10% FBS, penicillin (100 U/mL) and streptomycin (100 mg/mL)) per well. Eight wells were left empty for blank controls. The plates were incubated (37° C., 5% $CO_2$) overnight to allow the cells to attach to the wells. WST-1 proliferation reagent (Roche) was added to the cells (10 µL per well) and continued to incubate for 1-2 h at 37° C. Plates were checked visually by comparing the colour of wells with media without cells (colour remained pink) with wells contained untreated cells (colour is orange). When a clear difference could be seen by naked eye, results were read by spectrophotometer at 490 nm. Cytotoxicity (%) was determined using the following formula: Cytotoxicity (%)=(1−[Compounds ($OD_{490}$)−Background ($OD_{490}$)]/[Control ($OD_{490}$)−Background ($OD_{490}$)])×100.

Kinase Toxicity

Figure 6:
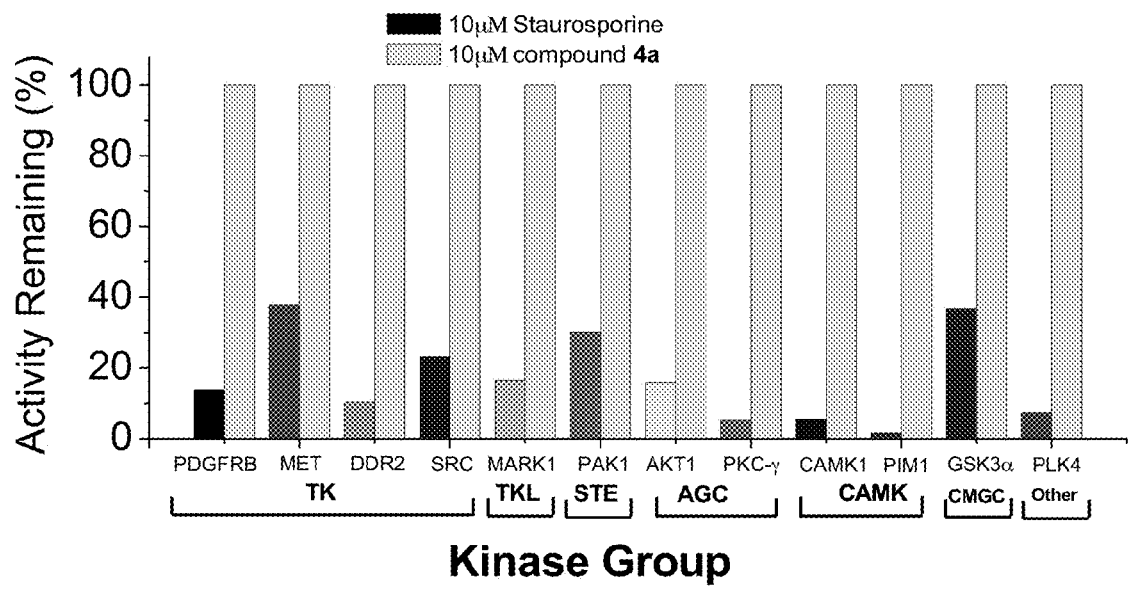
FIG. 6 is a graph of kinase profiling results showing that compound 4a (a TLR3 inhibitor) at 10 μM did not significantly affect activities of representative kinases.

As shown in FIG. 6, kinases profiling studies of a TLR3 inhibitor, compound 4a (10 µM), did not significantly affect activities of various representative kinases.

Animal Model In Vivo Test of Endothelial Dysfunction and Atherosclerosis

Endothelial dysfunction and atherosclerosis are chronic inflammatory diseases characterized by activation of the innate and acquired immune system. Zimmer, S. et al., Circ. Res., 2011, 108, 1358-1366. It is believed that specialized protein receptors of the innate immune system recognize products of microorganisms and endogenous ligands such as nucleic acids. TLR3 detects long double-stranded RNA and is abundantly expressed in endothelial cells. It has been shown that TLR3 stimulation not only induces endothelial dysfunction but also enhances the formation of atherosclerotic plaques in the mice. Id. Monocyte chemoattractant protein-1 (MCP-1) and RANTES (Regulated upon Activation, Normal T cell Expressed and presumably Secreted) are two of the cytokines that have been shown to respond to TLR3 stimulation. MCP-1 is believed to be produced predominantly by macrophages and endothelial cells and has shown to be a potent chemotactic factor for monocytes. Expression of this proinflammatory chemokine has been shown to increase in atherosclerotic lesions. Kanda, H. et al., J. Clin. Invest., 2006, 116, 1494-1505. RANTES, also known as CCL5 (Chemokine (C—C motif) ligand 5), is a member of the "CC" subfamily of chemokines. It has been shown to play a primary role in the inflammatory immune response via its ability to chemoattract leukocytes and modulate their function. Kim, M. O. et al., J. Neurochem. 2004, 90, 297-308. It has also been shown that antagonism of MCP-1 and RANTES receptors can reduce atherosclerotic. Kanda, H. et al.; J. Clin. Invest., 2006, 116, 1494-1505 and Veillard, N. R. et al., Circ. Res., 2004, 94, 253-261.

Figure 7:
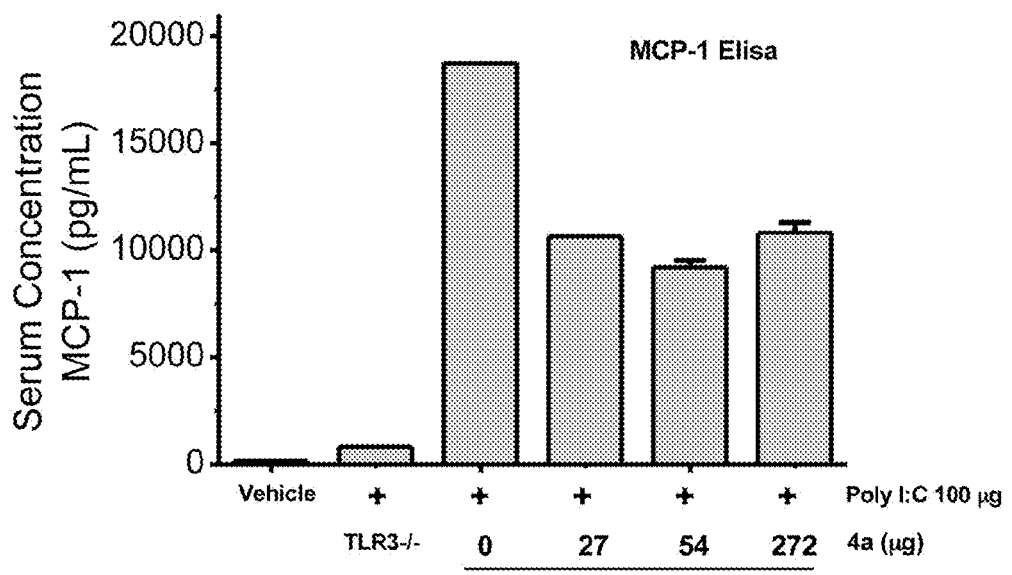
FIG. 7 is a graph showing the result of animal model in vivo test. Wild-type mice were treated with a single 100 μg poly IC i.v. injection and investigated the serum concentration of MCP-1 4 hours after treatment. As expected poly IC led to a significant increase in MCP-1, only in wild-type but not TLR3-/- mice. Pretreatment with compound 4a 30 minutes prior to poly IC application decreased MCP-1 production by about 50%.

Wild-type mice were treated with a single 100 μg of poly IC i.v. injection and the serum concentration of MCP-1 was investigated 4 hours after the treatment. As shown in FIG. 7, administration of poly IC resulted in a significant increase in MCP-1, only in wild-type but not TLR3−/− mice. Pretreatment with compound 4a at various concentrations 30 minutes prior to poly I:C application decreased MCP-1 production by about 50%.

Figure 8:
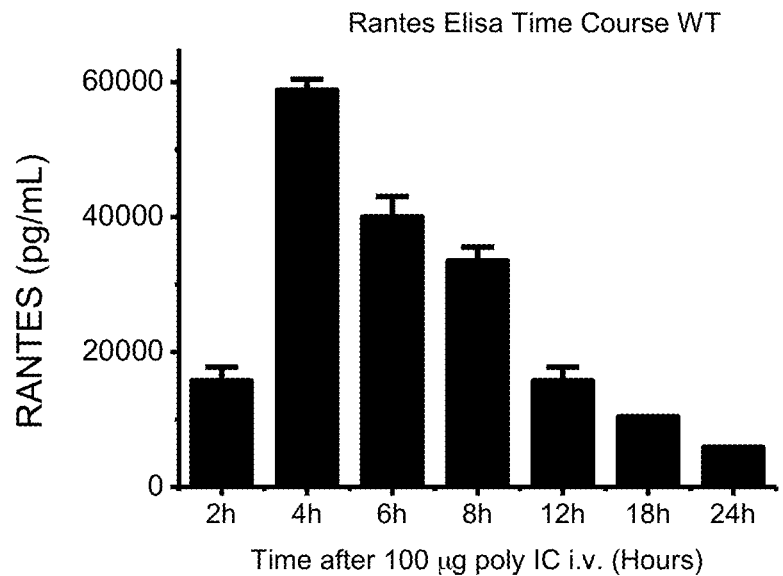
FIG. 8 is a graph showing response of cytokine RANTES to TLR3 stimulation. It peak approximately 4 h after i.v. injection.
Figure 9:
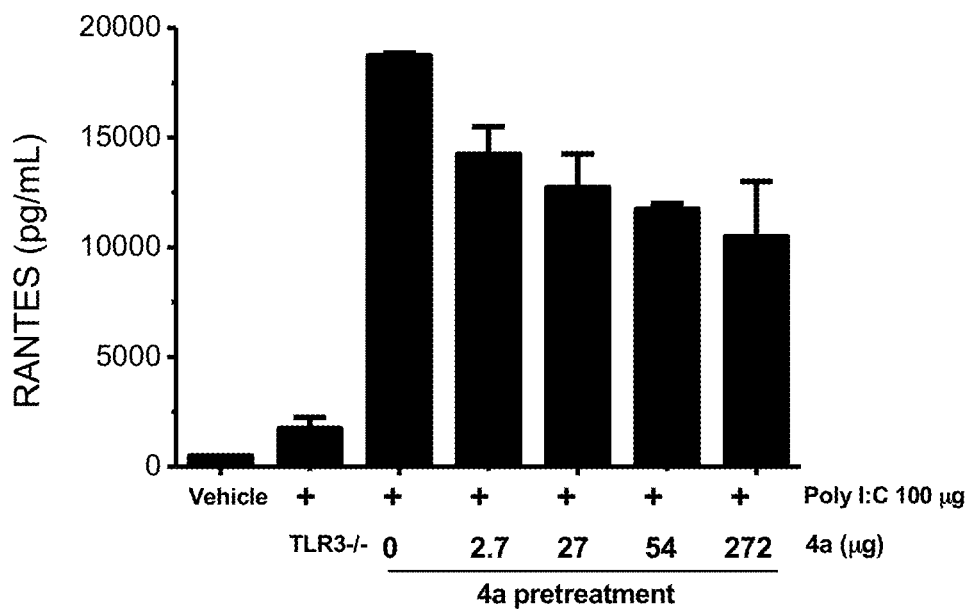
Figure 10:
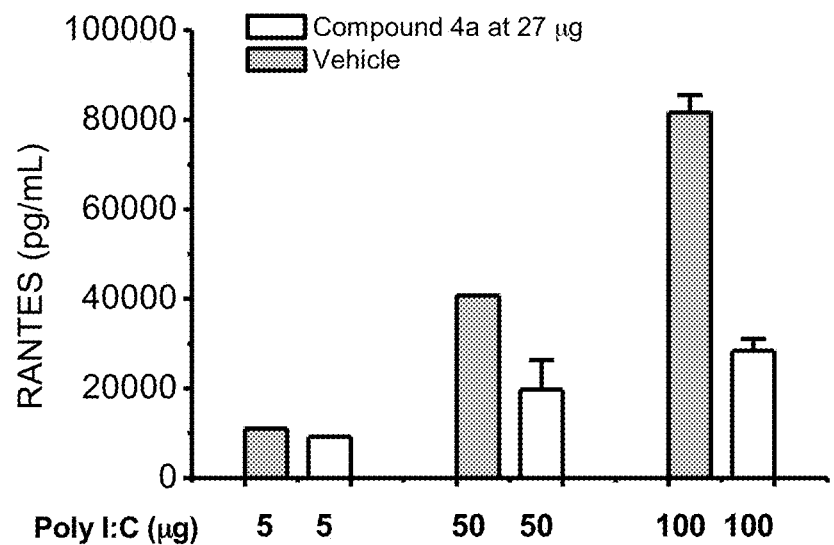
FIG. 10 is a graph showing pretreatment with 27 μg of compound 4a results in decreased RANTES production with increasing poly IC doses.

RANTES is another cytokine that has been shown to respond to TLR3 stimulation. As shown in FIG. 8, RANTES peaked approximately 4 h after i.v. injection of poly IC. However, pretreatment with compound 4a resulted in decrease of RANTES in a dose-dependent manner. FIG. 9. As shown in FIG. 10, RANTES production increased relatively proportionally with increasing poly IC doses ("vehicle"). However, pretreatment with 27 μg of compound 4a resulted in a significant decrease in RANTES production.

Prostate Cancer Treatment/Diagnosis

Xenotropic murine leukemia-related retrovirus (XMRV) is a recently discovered retrovirus that has been linked to human prostate cancer. Schlaberga, R. et al., *Proc. Natl. Acad. Sci. U.S.A.*, 2009, 106, 16351-16356. It is estimated that XMRV infection affects a large fraction of the world population, with prostate cancer affecting one in six men. Hayat, M. J. et al., *Oncologist*, 2007, 12, 20-37. Understanding the role of XMRV in prostate cancer tumorigenesis opens up opportunities to develop new diagnostic markers as well as new methods to prevent and treat this cancer with antiretroviral therapies or vaccines. Schlaberga, R. et al.; *Proc. Natl. Acad. Sci. U.S.A.*, 2009, 106, 16351-16356. The present inventors have discovered that TLR3 inhibitors of the invention efficiently suppressed the activity of XMRV to induce interferon γ-induced protein 10 (i.e., IP-10, also known as C—X—C motif chemokine 10 or CXCL10) production. Such results indicate TLR3 inhibitors of the invention can be used to treat and/or prevent prostate cancer.

Figure 11:
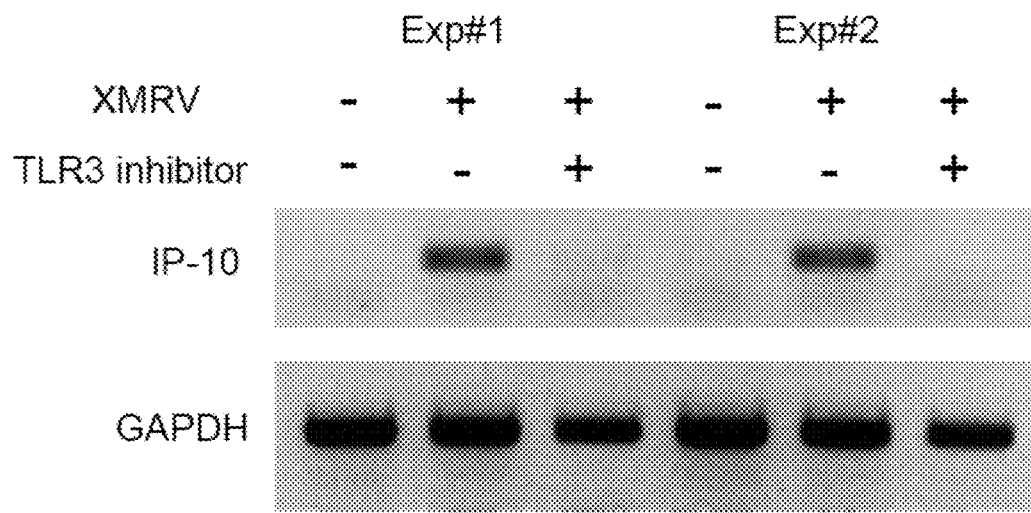
FIG. 11 is an electrophoresis slide showing inhibition of XMRV-induced (xenotropic murine leukemia virus-related virus) IP-10 (interferon gamma-induced protein 10) production. The RNA isolated from LNCaP (human prostatic carcinoma cell line) cells infected with XMRV in the presence or absence of compound 4a (50 μM) was subjected to RT-PCR detecting IP-10 mRNA. The GAPDH was used for the internal control.
Figure 12:
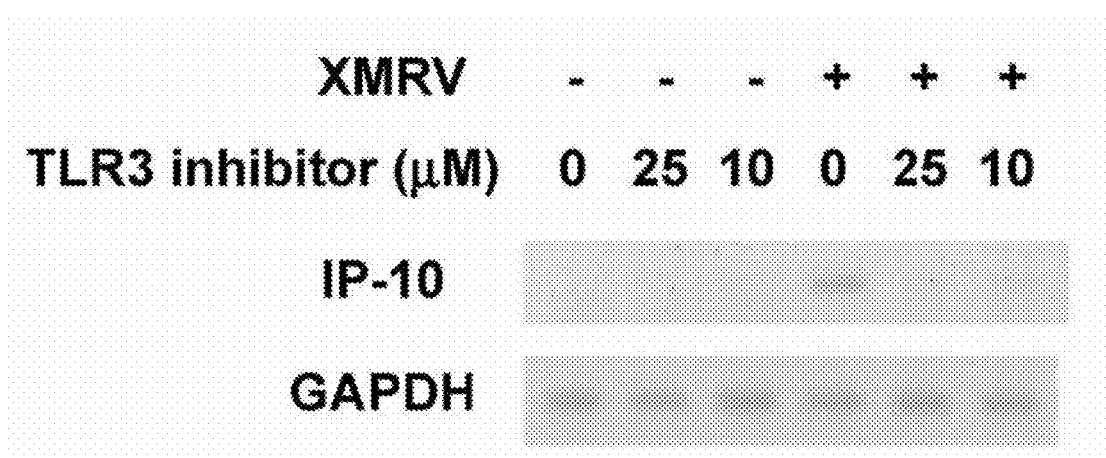
FIG. 12 is an electrophoresis slide showing inhibition of XMRV-induced IP-10/CXCL10 production by compound 4a. The RNA isolated from LNCaP cells infected with XMRV in the presence or absence of compound 4a (10 and 25 μM) was subjected to RT-PCR designed to detect IP-10/CXCL10 mRNA. GAPDH was used as the internal control. Representative data from three independent experiments are shown.

The RNA isolated from LNCaP (human prostatic carcinoma cell line) cells infected with XMRV in the presence or absence of a TLR3 inhibitor compound 4a (50 μM) was subjected to RT-PCR detecting IP-10 mRNA. The Glyceraldehyde 3-phosphate dehydrogenase (GAPDH) was used for the internal control. As shown in FIG. 11, compound 4a inhibits XMRV-induced IP-10 production. FIG. 12 shows the results of inhibition of XMRV-induced IP-10/CXCL10 production by compound 4a at 10 and 25 μM.

Vascular Repair

Mice were subjected to a 4 mm long electric denudation of the left common carotid artery. These C57B1/6J littermates were then treated with 100 μg of poly IC or vehicle (NaCl 0.9%) via i.v. injection every 48 hours for five days. Half of the mice in each group were also treated with 27 μg compound 4a or vehicle (DMSO) via i.p. injection every 48 hours. The mice were then sacrificed and aortic arch including both common carotid arteries excised. The remaining endothelial lesion was visualized using Evan's blue staining.

Figure 13:
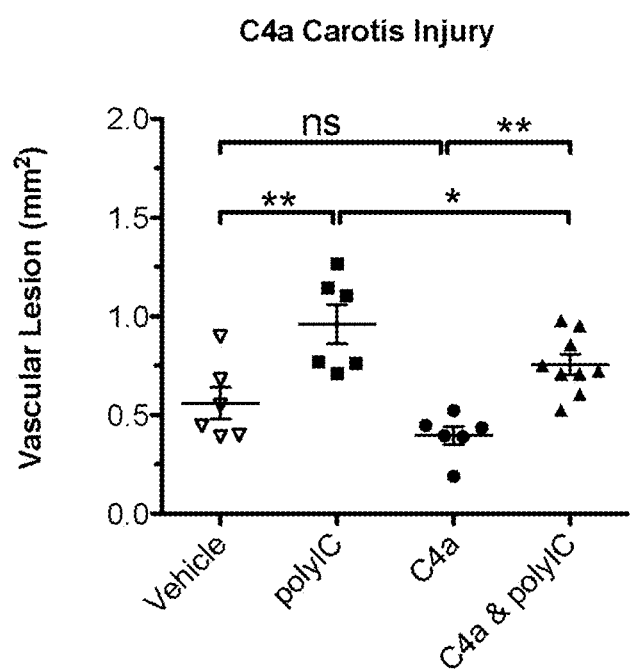
FIG. 13 is a graph showing that compound 4a significantly improves poly IC-induced impaired re-endothelialization.

As shown in FIG. 13, compound 4a significantly improved poly IC-induced impaired re-endothelialization. The present inventors have demonstrated that this is an important TLR3 dependent biological effect. See, for example, Zimmer, S. et al., *Circ. Res.* 2011, 108, 1358-1366. These results show that TLR3 inhibitors, such as compound 4a, significantly improve vascular (endothelial) repair/function.

Synthesis of (R)-phenylalanine tert-butyl ester (A1)

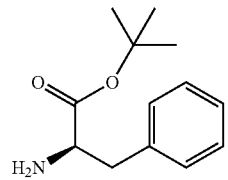

To a solution of D-phenylalanine (1.651 g, 10.0 mmol) in tert-butyl acetate (20 mL) at 0° C., was slowly added HClO₄ (0.85 mL, 15 mmol). The reaction mixture was stirred at room temperature for 12 h then washed with H₂O (25 mL) and 1.0 M HCl solution (15 mL). The resultant aqueous solution was adjusted to pH 9 by addition of 10% K₂CO₃ solution, and then extracted with dichloromethane (3×10 mL). The combined organic phases were dried with anhydrous Na₂SO₄, filtered and concentrated to give an oil. This was purified by flash chromatography on silica gel, using a grading of ethyl acetate/hexane ((1:5) to (2:5)), to give A1 as a colorless oil; (2.020 g, 89.3%). Spectral data were in accordance with those published. $[\alpha]_D^{25}$: −39.5 (c=0.33, CHCl₃); ¹H-NMR (300 MHz, CDCl₃): δ 7.35-7.29 (m, 2H), 7.27-7.22 (m, 3H), 3.63 (dd, J=6.0, 9.0 Hz, 1H), 3.09-3.02 (m, 1H), 2.89-2.82 (m, 2H), 1.47 (s, 2H), 1.44 (s, 9H); ¹³C NMR (300 MHz, CDCl₃): δ 174.34, 137.57, 129.39, 128.41, 126.65, 81.12, 56.33, 41.29, 28.00; LRMS (ESI): calcd for: C₁₃H₁₉NO₂ [M+H]⁺=222.1, obsd [M+H]⁺=222.1, [M+Na]⁺=244.1, obsd [M+Na]⁺=244.1.

Synthesis of (S)-phenylalanine tert-butyl ester (B1)

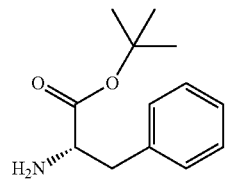

Following the A1 synthetic method, using L-phenylalanine (1.651 g, 10.0 mmol) instead of D-phenylalanine gave B1 as a colorless oil; (2.01 g, 88.9%). $[\alpha]_D^{25}$: +49.8 (c=0.62, CHCl₃); ¹H-NMR (300 MHz, CDCl₃): δ 7.35-7.28 (m, 2H), 7.27-7.22 (m, 3H), 3.63 (dd, J=6.0, 9.0 Hz, 1H), 3.09-3.02 (m, 1H), 2.89-2.82 (m, 2H), 1.44 (m, 11 H). ¹³C NMR (300 MHz, CDCl₃): δ 174.34, 137.58, 129.38, 128.41, 126.64, 81.11, 56.33, 41.30, 28.00; LRMS (ESI): calcd for: C₁₃H₁₉NO₂ [M+H]⁺=222.1, obsd [M+H]=222.1, [M+Na]⁺=244.1.

Synthesis of (R)-tyrosine tert-butyl ester (A2)

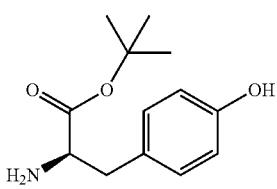

Following the A1 synthetic method, using D-tyrosine (1.812 g, 10.0 mmol) instead of D-phenylalanine gave A2 as colorless oil; (1.41 g, 60.2%). $[\alpha]_D^{25}$: +41.3 (c=0.45, CHCl$_3$); $^1$H-NMR (300 MHz, CDCl$_3$): δ 7.06 (s, 1H), 7.04 (s, 1H), 6.70 (s, 1H), 6.67 (s, 1H), 3.61 (m, 1H), 3.05-2.98 (m, 1H), 3.82-2.75 (m, 1H), 1.47 (s, 9H); $^{13}$C NMR (300 MHz, CDCl$_3$): δ 174.08, 155.44, 130.39, 127.92, 115.69, 81.65, 55.99, 39.81, 28.04; LRMS (ESI): calcd for: C$_{13}$H$_{19}$NO$_3$ [M+H]$^+$=238.1, obsd [M+H]$^+$=238.1, [M+Na]$^+$=260.1, obsd [M+Na]$^+$=260.1.

Synthesis of (S)-tyrosine tert-butyl ester (B2)

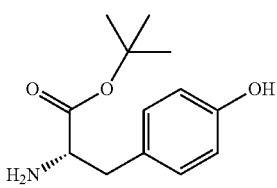

Following the A1 synthetic method, using L-tyrosine (1.812 g, 10.0 mmol) instead of D-phenylalanine gave B2 as colorless oil; (1.42 g, 60.8%). $[\alpha]_D^{25}$: −55.5 (c=0.23, CHCl$_3$); $^1$H-NMR (300 MHz, CDCl$_3$): δ 7.08 (s, 1H), 7.04 (s, 1H), 6.71 (s, 1H), 6.68 (s, 1H), 3.61 (m, 1H), 3.04-2.98 (m, 1H), 3.82-2.75 (m, 1H), 1.47 (s, 9H); $^{13}$C NMR (300 MHz, CDCl$_3$): δ 174.02, 155.55, 130.40, 127.76, 115.73, 81.68, 55.95, 39.77, 28.03; LRMS (ESI): calcd for: C$_{13}$H$_{19}$NO$_3$ [M+H]$^+$=238.1, obsd [M+H]$^+$=238.1, [M+Na]$^+$=260.1, obsd [M+Na]$^+$=260.1.

Benzo[b]thiophene-2-carbonyl chloride (3)

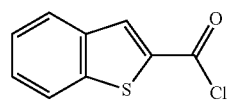

Thianaphthene-2-carboxylic acid (356.42 mg, 2 mmol) was suspended in dry toluene (6 mL), thionyl chloride (4.4 mL, 60 mmol) and DMF (0.05 mL) were added at room temperature, and then the mixture was refluxed 8 h.[4] The volatiles were removed at reduced pressure gave benzo[b]thiophene-2-carbonyl chloride as a yellow power. Purified by flash chromatography on silica gel, using ethyl acetate/hexane (1:9) as eluent, give 3 as a white power (393.64 mg, 94.9%). Spectral data were in accordance with those published. $^1$H-NMR (300 MHz, CDCl$_3$): δ 8.31 (s, 1H), 7.04-7.89 (m, 2H), 7.60-7.46 (m, 2H. $^{13}$C NMR (300 MHz, CDCl$_3$): δ 161.14, 144.07, 138.05, 136.59, 135.89, 128.75, 126.68, 125.66, 122.91.

(R)-2-(benzo[b]thiophene-2-carboxamido)-3-phenyl-propanoic acid (1a)

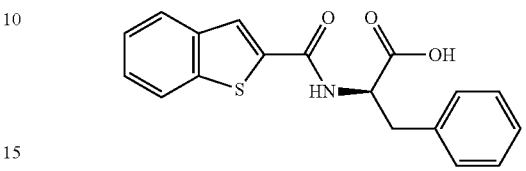

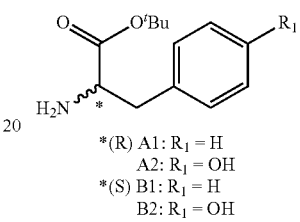

*(R) A1: R$_1$ = H
 A2: R$_1$ = OH
*(S) B1: R$_1$ = H
 B2: R$_1$ = OH

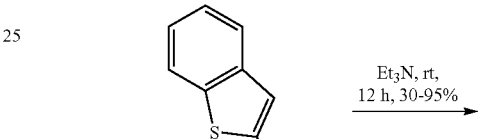

Et$_3$N, rt,
12 h, 30-95%

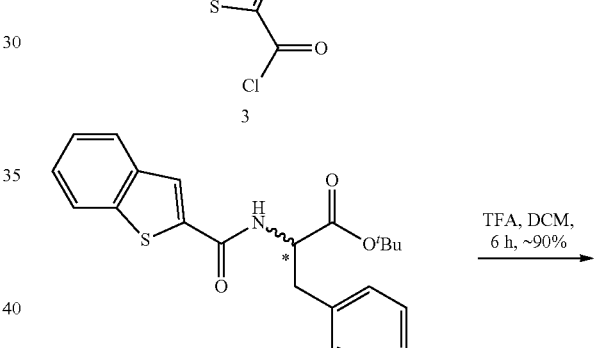

TFA, DCM,
6 h, ~90%

*(R) 1a-$^t$Bu: R$_1$ = H
 9a-$^t$Bu: R$_1$ = OH
*(S) 1b-$^t$Bu: R$_1$ = H
 9b-$^t$Bu: R$_1$ = OH

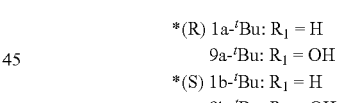

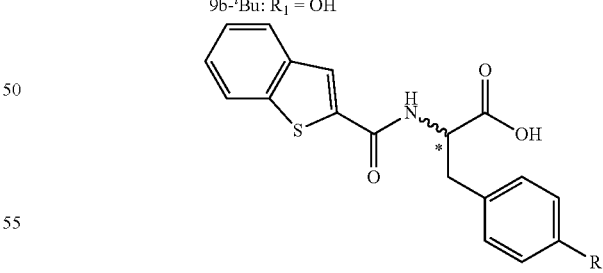

*(R) 1a: R$_1$ = H
 9a: R$_1$ = OH
*(S) 1b: R$_1$ = H
 9b: R$_1$ = OH

Method A

To a solution of D-phenylalanine tert-butyl ester (110.65 mg, 0.5 mmol) in dry dichloromethane (3 mL) at 0° C. was added triethylamine (0.086 mL, 0.55 mmol) and benzo[b]thiophene-2-carbonyl chloride (98.33 mg, 0.5 mmol). The reaction mixture was stirred at room temperature overnight and then washed with H₂O (3×15 mL) and the organic extracts were dried with Na₂SO₄ and concentrated under reduced pressure. Purified by flash chromatography on silica gel, using ethyl acetate/hexane (1:9) as eluent, give 1a-ᵗBu as colorless oil (176.43 mg, 92.5%). $[\alpha]_D^{25}$: −38.8 (c=0.18, CHCl₃); ¹H-NMR (300 MHz, CDCl₃): δ 7.88-7.82 (m, 2H), 7.75 (d, J=0.9 Hz, 1H), 7.47-7.38 (m, 2H), 7.35-7.27 (m, 3H), 7.25-7.21 (m, 2H), 6.77 (d, J=7.5 Hz, 1H), 5.03-4.96 (m, 1H), 3.27 (m, 2H), 1.47 (s, 9H); ¹³C NMR (300 MHz, CDCl₃): δ 170.51, 161.58, 140.99, 139.05, 138.07, 136.01, 129.65, 128.45, 127.09, 126.39, 125.38, 125.11, 124.90, 122.70, 82.81, 54.02, 38.05, 28.02; HRMS (ESI): calcd for: $C_{22}H_{23}NO_3S$ [M+Na]⁺=404.1304, obsd [M+Na]⁺=404.1291.

Then 1a-ᵗBu (95.37 mg, 0.25 mmol) was dissolved in 2 mL of CH₂Cl₂ and 2 mL TFA was add under argon. The reaction mixture was stirred at room temperature for 12 h (TLC monitor). The solvent was removed under reduce pressure and the crude compound was purified by flash chromatography on silica gel, using HOAc/ethyl acetate (1:100) as the eluent, gave 1a (73.29 mg, 90.1%); $[\alpha]_D^{25}$: −25.9 (c=0.21, CHCl₃). ¹H-NMR (300 MHz, CDCl₃): δ 10.55 (bs, 1H), 7.83-7.72 (m, 3H), 7.45-7.34 (m, 2H), 7.32-7.21 (m, 5H), 6.83 (d, J=7.5 Hz, 1H), 5.12 (m, 1H), 3.41-3.25 (m, 2H); ¹³C NMR (300 MHz, CDCl₃): δ 175.13, 162.59, 141.05, 138.91, 136.97, 135.51, 129.44, 128.75, 127.34, 126.29, 125.27, 124.99, 124.94, 122.66, 53.82, 37.35; HRMS (ESI): calcd for: $C_{18}H_{15}NO_3S$ [M+H]⁺=326.0830, obsd [M+H]⁺=326.0845.

Method B

To a solution of A1 (110.65 mg, 0.5 mmol) in dry dichloromethane (3 mL) was added HATU (171.09 mg, 0.45 mmol), DIPEA (0.174 mL, 1 mmol) and benzo[b]thiophene-2-carboxylic acid (93.56 mg, 0.525 mmol). The reaction mixture was stirred at room temperature overnight and concentrated under reduced pressure, using ethyl acetate/hexane (1:9) as eluent, give 1a-ᵗBu as a colorless oil (181.01 mg, 94.9%). Then 1a-ᵗBu (95.37 mg, 0.25 mmol) was dissolved in 2 mL of CH₂Cl₂ and 2 mL TFA was add under argon. The reaction mixture was stirred at room temperature for 12 h (TLC monitor). The solvent was removed under reduce pressure and the crude compound was purified by flash chromatography on silica gel, using HOAc/ethyl acetate (1:100) as the eluent, gave 1a (73.29 mg, 90.1%).

(S)-2-(benzo[b]thiophene-2-carboxamido)-3-phenyl-propanoic acid (1b)

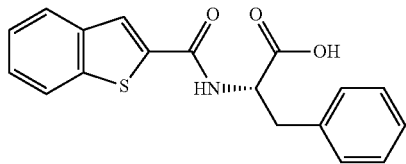 [SMILES: O=C(N[C@@H](Cc1ccccc1)C(=O)O)c1cc2ccccc2s1]

Following the general method B, using B1 (110.65 mg, 0.5 mmol) instead of A1 gave 1b-ᵗBu as a colorless oil; (182.55 mg, 95.6%). $[\alpha]_D^{25}$: +41.6 (c=0.31, CHCl₃); ¹H-NMR (300 MHz, CDCl₃): δ 10.47 (bs, 1H), 7.78-7.69 (m, 3H), 7.47-7.38 (m, 2H), 7.42-7.29 (m, 3H), 7.27-7.20 (m, 4H), 6.89 (d, J=8.2 Hz, 1H), 5.07 (m, 1H), 3.38-3.21 (m, 2H); ¹³C NMR (300 MHz, CDCl₃): δ 175.24, 162.64, 141.02, 138.90, 137.01, 135.64, 129.39, 128.73, 127.28, 126.58, 126.24, 125.25, 124.94, 122.62, 53.98, 37.31; HRMS (ESI): calcd for: $C_{18}H_{15}NO_3S$ [M+Na]⁺=348.0651, obsd [M+Na]⁺=348.0665.

Then 1b-ᵗBu (95.37 mg, 0.25 mmol) was dissolved in 2 mL of CH₂Cl₂ and 2 mL TFA was add under argon. The reaction mixture was stirred at room temperature for 12 h (TLC monitor). The solvent was removed under reduce pressure and the crude compound was purified by flash chromatography on silica gel, using HOAc/ethyl acetate (1:100) as the eluent, gave 1a; (74.11 mg, 91.1%). $[\alpha]_D^{25}$: +26.1 (c=0.22, CHCl₃); ¹H-NMR (300 MHz, CDCl₃): δ 10.47 (bs, 1H), 7.78-7.69 (m, 3H), 7.47-7.38 (m, 2H), 7.42-7.29 (m, 3H), 7.27-7.20 (m, 4H), 6.89 (d, J=8.2 Hz, 1H), 5.07 (m, 1H), 3.38-3.21 (m, 2H); ¹³C NMR (300 MHz, CDCl₃): δ 175.24, 162.64, 141.02, 138.90, 137.01, 135.64, 129.39, 128.73, 127.28, 126.58, 126.24, 125.25, 124.94, 122.62, 53.98, 37.31; HRMS (ESI): calcd for: $C_{18}H_{15}NO_3S$ [M+Na]⁺=348.0651, obsd [M+Na]⁺=348.0665

(R)-2-(benzo[b]thiophene-2-carboxamido)-3-(4-hydroxyphenyl)propanoic acid (9a)

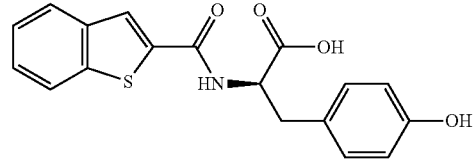 [SMILES: O=C(N[C@H](Cc1ccc(O)cc1)C(=O)O)c1cc2ccccc2s1]

Following general method B, to a solution of A2 (237.29 mg, 1.0 mmol) in dry dichloromethane (5 mL) at 0° C. was added triethylamine (0.172 mL, 1.1 mmol) and 3 (196.65 mg, 1.0 mmol). The reaction mixture was stirred at room temperature overnight and then washed with H₂O (3×15 mL) and the organic extracts were dried with Na₂SO₄ and concentrated under reduced pressure. Purified by flash chromatography on silica gel, using ethyl acetate/hexane (2:5) as eluent, give 9a-ᵗBu as colorless oil (120.44 mg, 30.3%). $[\alpha]_D^{25}$: +41.1 (c=0.41, CHCl₃); ¹H-NMR (300 MHz, CDCl₃): δ 7.87-7.82 (m, 2H), 7.77 (s, 1H), 7.47-7.38 (m, 2H), 7.08-7.05 (m, 2H), 6.79-6.71 (m, 3H), 4.98-4.92 (m, 1H), 3.25-3.12 (m, 2H), 1.49 (s, 9H); ¹³C NMR (300 MHz, CDCl₃): δ 170.71, 161.73, 155.01, 141.99, 139.03, 137.84, 130.74, 127.59, 126.45, 125.58, 125.15, 124.93, 122.70, 115.38, 82.97, 54.13, 37.25, 28.04. HRMS (ESI): calcd for: $C_{22}H_{23}NO_4S$ [M+Na]⁺=420.1240, obsd [M+Na]⁺=420.1257.

Then 9a-ᵗBu (99.37 mg, 0.25 mmol) was dissolved in 2 mL of CH₂Cl₂ and 2 mL TFA was add under argon. The reaction mixture was stirred at room temperature for 12 h (TLC monitor). The solvent was removed under reduce pressure and the crude compound was purified by flash chromatography on silica gel, using HOAc/ethyl acetate (1:100) as the eluent, gave 9a; (75.78 mg, 88.8%). $[\alpha]_D^{25}$: +22.7 (c=0.21, CHCl₃); ¹H-NMR (300 MHz, acetone-d₆): δ 8.04 (s, 1H), 7.99-7.90 (m, 2H), 7.49-7.40 (m, 2H), 7.20-7.17 (m, 2H), 6.78-6.75 (m, 2H), 4.91-4.84 (m, 1H), 3.30-3.06 (m, 2H); ¹³C NMR (300 MHz, acetone-d₆): δ 161.56, 156.11, 140.93, 139.46, 130.25, 128.01, 126.24, 125.12, 124.88, 124.81, 122.57, 115.09, 36.22; HRMS (ESI): calcd for: $C_{18}H_{15}NO_4S$ [M+Na]⁺=364.0614, obsd [M+Na]⁺=364.0626.

(S)-tert-butyl 2-(benzo[b]thiophene-2-carboxamido)-3-(4-hydroxyphenyl)propanoate (9b)

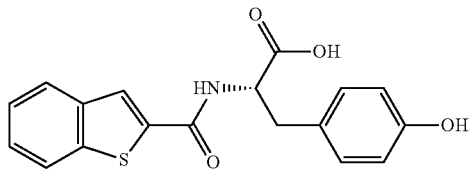 [SMILES: O=C(N[C@@H](Cc1ccc(O)cc1)C(=O)O)c1cc2ccccc2s1]

Following the 9a synthetic method, using B2 (237.29 mg, 1.0 mmol) instead of A2 gave 9b-$^t$Bu as colorless oil; (124.03 mg, 31.2%). $[\alpha]_D^{25}$: −44.6 (c=0.30, CHCl$_3$); $^1$H-NMR (300 MHz, CDCl$_3$): δ 7.86-7.77 (m, 3H), 7.46-7.36 (m, 2H), 7.28 (s, 1H), 7.06-7.03 (m, 2H), 7.78-7.75 (m, 2H), 6.29 (s, 1H), 4.99-4.92 (m, 1H), 3.23-3.10 (m, 2H), 1.48 (s, 9H); $^{13}$C NMR (300 MHz, CDCl$_3$): δ 178.83, 161.85, 155.21, 141.00, 139.02, 137.73, 130.68, 127.34, 125.67, 125.17, 124.93, 122.69, 115.43, 83.04, 54.17, 37.27, 28.03; HRMS (ESI): calcd for: C$_{22}$H$_{23}$NO$_4$S [M+Na]$^+$=420.1244, obsd [M+Na]$^+$=420.1240.

Then 9b-$^t$Bu (99.37 mg, 0.25 mmol) was dissolved in 2 mL of CH$_2$Cl$_2$ and 2 mL TFA was add under argon. The reaction mixture was stirred at room temperature for 12 h (TLC monitor). The solvent was removed under reduce pressure and the crude compound was purified by flash chromatography on silica gel, using HOAc/ethyl acetate (1:100) as the eluent, gave 9b; (76.04 mg, 89.1%). $[\alpha]_D^{25}$: −21.6 (c=0.27, CHCl$_3$); $^1$H-NMR (300 MHz, acetone-d$_6$): δ 8.03-7.89 (m, 3H), 7.49-7.39 (m, 2H), 7.19-7.16 (m, 2H), 6.76-6.73 (m, 2H), 4.85-4.80 (m, 1H), 3.29-3.06 (m, 2H); $^{13}$C NMR (300 MHz, acetone-d$_6$): δ 172.79, 161.58, 156.13, 140.92, 139.47, 130.29, 128.11, 126.22, 125.14, 124.90, 124.79, 122.55, 115.13, 78.31, 54.65, 36.29; HRMS (ESI): calcd for: C$_{18}$H$_{15}$NO$_4$S [M+Na]$^+$=364.0618, obsd [M+Na]$^+$=364.0614.

(R)-2-(3-chloro-6-methylbenzo[b]thiophene-2-carboxamido)-3-phenylpropanoic acid (2a)

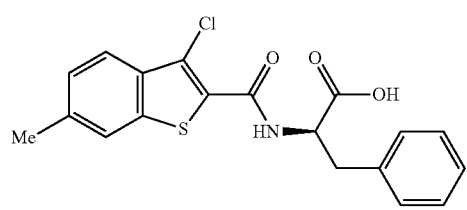

Following general method B, to a solution of A1 (110.65 mg, 0.5 mmol) in dry dichloromethane (3 mL) was added HATU (171.09 mg, 0.45 mmol), DIPEA (0.174 mL, 1 mmol) and 3-chloro-6-methylbenzo[b]thiophene-2-carboxylic acid (113.34 mg, 0.50 mmol). The reaction mixture was stirred at room temperature overnight and concentrated under reduced pressure gave an yellow oil. Then the oil was dissolved in 2 mL of CH$_2$Cl$_2$ and 2 mL TFA was add under argon. The reaction mixture was stirred at room temperature for 12 h (TLC monitor). The solvent was removed under reduce pressure and the crude compound was purified by flash chromatography on silica gel, using HOAc/ethyl acetate (1:100) as the eluent, gave 2a; (178.51 mg, 95.5%). $[\alpha]_D^{25}$: −31.7 (c=0.36, CHCl$_3$); $^1$H-NMR (300 MHz, acetone-d$_6$): δ 7.80-7.75 (m, 3H), 7.41-7.24 (m, 6H), 5.03-4.97 (m, 1H), 3.44-3.26 (m, 2H), 2.50 (s, 3H); $^{13}$C NMR (300 MHz, acetone-d$_6$): δ 171.57, 159.83, 138.30, 138.05, 136.67, 134.65, 131.57, 129.50, 128.39, 127.54, 126.87, 122.57, 122.51, 118.78, 54.03, 36.85, 20.73; HRMS (ESI): calcd for: C$_{19}$H$_{16}$ClNO$_3$S [M−H]$^-$=372.0467, obsd [M−H]$^-$=472.0484.

(S)-2-(3-chloro-6-methylbenzo[b]thiophene-2-carboxamido)-3-phenylpropanoic acid (2b)

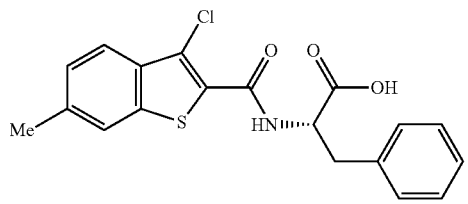

Following the 2a synthetic method, using B1 (110.65 mg, 0.5 mmol) instead of A1 gave 2b white powder; (179.63 mg, 96.1%). $[\alpha]_D^{25}$: +23.9 (c=0.29, CHCl$_3$); $^1$H-NMR (300 MHz, acetone-d$_6$): δ 7.76-7.72 (m, 3H), 7.39-7.22 (m, 6H), 5.04-4.98 (m, 1H), 3.44-3.26 (m, 2H), 2.48 (s, 3H); $^{13}$C NMR (300 MHz, acetone-d$_6$): δ 171.81, 159.86, 138.26, 138.03, 136.71, 134.63, 131.56, 129.53, 128.38, 127.49, 126.86, 122.53, 122.49, 118.80, 54.13, 36.88, 20.75; HRMS (ESI): calcd for: C$_{19}$H$_{16}$ClNO$_3$S [M−H]$^-$=372.0467, obsd [M−H]$^-$=472.0475.

(R)-2-(3,6-dichlorobenzo[b]thiophene-2-carboxamido)-3-phenylpropanoic acid (3a)

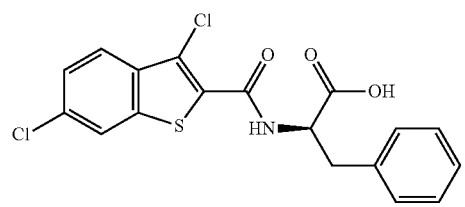 [SMILES: O=C(N[C@H](Cc1ccccc1)C(=O)O)c1sc2cc(Cl)ccc2c1Cl]

Following the 2a synthetic method, using 3,6-dichlorobenzo[b]thiophene-2-carboxylic acid (123.55 mg, 0.5 mmol) instead of 3-chloro-6-methylbenzo[b]thiophene-2-carboxylic acid gave 3a as a white powder; (182.94 mg, 92.8%). $[\alpha]_D^{25}$: −23.2 (c=0.24, CHCl$_3$); $^1$H-NMR (300 MHz, CDCl$_3$): δ 8.79 (s, 1H), 7.78 (d, J=1.5 Hz, 1H), 7.71 (d, J=8.7 Hz, 1H), 7.59 (d, J=6.9 Hz, 1H), 7.42 (dd, J=1.8, 8.7 Hz, 1H), 7.37-7.25 (m, 5H), 5.16-5.14 (m, 1H), 3.41-3.28 (m, 2H); $^{13}$C NMR (300 MHz, CDCl$_3$): δ 175.51, 160.41, 138.97, 135.33, 135.18, 134.21, 132.38, 129.47, 128.82, 127.52, 126.51, 124.16, 122.38, 119.64, 54.12, 37.28; HRMS (ESI): calcd for: C$_{18}$H$_{13}$Cl$_2$NO$_3$S [M−H]$^-$=391.9920, obsd [M−H]$^-$=391.9921.

(S)-2-(3,6-dichlorobenzo[b]thiophene-2-carboxamido)-3-phenylpropanoic acid (3b)

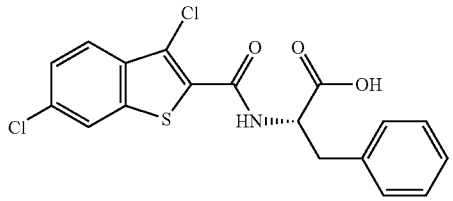

Following the 2a synthetic method, using B1 (110.65 mg, 0.5 mmol) instead of A1 gave 3b as a white powder (183.93 mg, 93.3%). $^1$H-NMR (300 MHz, CDCl$_3$): δ 9.23 (s, 1H), 7.78 (d, J=1.8 Hz, 1H), 7.71 (d, J=8.7 Hz, 1H), 7.59 (d, J=7.2 Hz, 1H), 7.42 (dd, J=1.8, 8.7 Hz, 1H), 7.37-7.25 (m, 5H), 5.16-5.14 (m, 1H), 3.39-3.33 (m, 2H). $[α]_D^{25}$: +17.5 (c=0.16, CHCl$_3$). $^{13}$C NMR (300 MHz, CDCl$_3$): δ 175.54, 160.40, 138.96, 135.32, 135.19, 134.20, 132.40, 129.47, 128.82, 127.51, 126.55, 124.15, 122.37, 119.62, 54.07, 37.28. HRMS (ESI): calcd for: C$_{18}$H$_{13}$Cl$_2$NO$_3$S [M−H]$^−$=391.9920, obsd [M−H]−=391.9916.

(R)-2-(3-chloro-6-fluorobenzo[b]thiophene-2-carboxamido)-3-phenylpropanoic acid (4a)

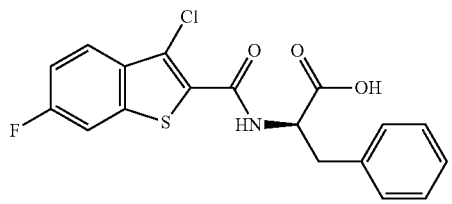 [SMILES: O=C(N[C@H](Cc1ccccc1)C(=O)O)c1sc2cc(F)ccc2c1Cl]

Following the 2a synthetic method, using 3-chloro-6-fluorobenzo[b]thiophene-2-carboxylic acid (115.32 mg, 0.5 mmol) instead of 3-chloro-6-methylbenzo[b]thiophene-2-carboxylic acid gave 4a as a white powder; (177.01 mg, 93.7%). $[α]_D^{25}$: −21.9 (c=0.37, CHCl$_3$); $^1$H-NMR (300 MHz, acetone-d$_6$): δ 7.95-7.76 (m, 3H), 7.44-7.22 (m, 6H), 5.04-4.97 (m, 1H), 3.45-3.26 (m, 2H); $^{13}$C NMR (300 MHz, acetone-d$_6$): δ 171.48, 163.90, 160.62, 159.50, 139.15, 136.67, 133.50, 129.50, 128.40, 126.89, 124.94, 118.57, 115.15, 114.82, 109.30, 108.95, 53.95, 36.78; HRMS (ESI): calcd for: C$_{18}$H$_{13}$ClFNO$_3$S [M+H]$^+$=378.0361, obsd [M+H]$^+$=378.0347.

(S)-2-(3-chloro-6-fluorobenzo[b]thiophene-2-carboxamido)-3-phenylpropanoic acid (4b)

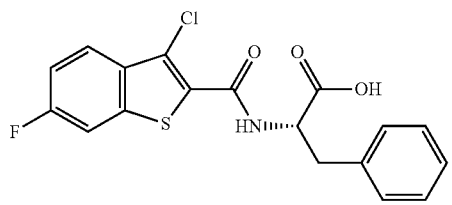 [SMILES: O=C(N[C@@H](Cc1ccccc1)C(=O)O)c1sc2cc(F)ccc2c1Cl]

Following the 4a synthetic method, using B1 (110.65 mg, 0.5 mmol) instead of A1 gave 4b as a white powder; (175.31 mg, 92.8%). $[α]_D^{25}$: +15.5 (c=0.38, CHCl$_3$); $^1$H-NMR (300 MHz, acetone-d$_6$): δ 8.03-7.77 (m, 3H), 7.44-7.25 (m, 6H), 5.03-4.97 (m, 1H), 3.45-3.26 (m, 2H); $^{13}$C NMR (300 MHz, acetone-d$_6$): δ 163.90, 160.62, 159.50, 139.01, 136.65, 133.57, 129.50, 128.40, 126.88, 124.94, 115.15, 114.82, 109.31, 108.96, 54.06, 36.79; HRMS (ESI): calcd for: C$_{18}$H$_{13}$ClFNO$_3$S [M+H]$^+$=378.0361, obsd [M+H]$^+$=378.0352.

3-chloro-6-(trifluoromethyl)benzo[b]thiophene-2-carbonyl chloride (5)

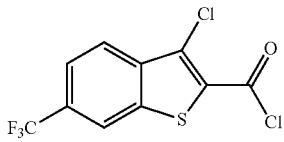 [SMILES: O=C(Cl)c1sc2cc(C(F)(F)F)ccc2c1Cl]

To a mixture of p-trifluoromethylcinnamic acid (864.64 mg, 4.0 mmol) and pyridine (0.045 mL, 0.56 mmol) was added approximately ⅓ of thionyl chloride (0.667 mL).$^6$ The mixture was heated to 140° C., and the rest of the thionyl chloride was added at a rate such as not to drop the temperature below 135° C. (40 min). The mixture was then heated at, 140-145° C. for an additional 12 h and concentrated unger reduce pressure. The mixture solid was dissolved in hot hexanes (20 mL) and decanted to separate pyridine hydrochloride. For recrystallizations from the solution afforded 5 as a yellow crystals; (277.56 mg, 23.2%). $^1$H-NMR (300 MHz, CDCl$_3$): δ 8.18-8.14 (m, 2H), 7.80 (dd, J=1.2, 8.4 Hz, 1H). $^{13}$C NMR (300 MHz, CDCl$_3$): δ 157.99, 139.70, 139.24, 132.54, 131.84, 131.41, 130.07, 125.59, 122.95, 120.61.

(R)-2-(3-chloro-6-(trifluoromethyl)benzo[b]thiophene-2-carboxamido)-3-phenylpropanoic acid (5a)

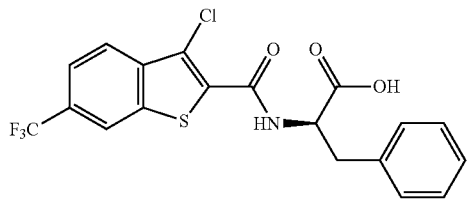 [SMILES: O=C(N[C@H](Cc1ccccc1)C(=O)O)c1sc2cc(C(F)(F)F)ccc2c1Cl]

Following general method B, to a solution of A1 (55.33 mg, 0.25 mmol) in dry dichloromethane (2 mL) at 0° C. was added triethylamine (0.043 mL, 0.28 mmol) and 5 (74.78 mg, 0.25 mmol). The reaction mixture was stirred at room temperature overnight and concentrated under reduced pressure. Then dissolved the oil mixture in 2 mL CH$_2$Cl$_2$ and 2 mL TFA was add under argon. The reaction mixture was stirred at room temperature for 12 h (TLC monitor). The solvent was removed under reduce pressure and the crude compound was purified by flash chromatography on silica gel, using HOAc/ethyl acetate (1:100) as the eluent, gave 5a; (100.64 mg, 94.1%). $[α]_D^{25}$: −21.1 (c=0.30, CHCl$_3$); $^1$H-NMR (300 MHz, CDCl$_3$): δ 8.12 (s, 1H), 7.93 (d, J=8.7 Hz, 1H), 7.71-7.61 (m, 2H), 7.37-7.26 (m, 5H), 6.83 (s, 1H), 5.17-5.15 (m, 1H), 3.45-3.30 (m, 2H); $^{13}$C NMR (300 MHz, CDCl$_3$): δ 175.31, 160.07, 139.09, 137.76, 135.24, 135.13, 129.90, 129.46, 128.84, 127.56, 125.63, 123.89, 122.16, 120.45, 120.40, 119.49, 54.09, 39.26, 29.70; HRMS (ESI): calcd for: C$_{19}$H$_{13}$ClF$_3$NO$_3$S [M−H]$^−$=426.0184, obsd [M−H]$^−$=426.0170.

(S)-2-(3-chloro-6-(trifluoromethyl)benzo[b]thiophene-2-carboxamido)-3-phenylpropanoic acid (5b)

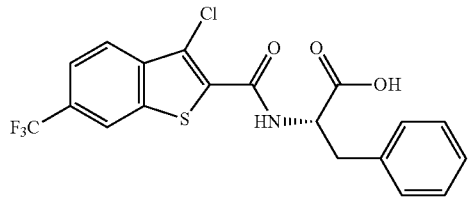

Following the 5a synthetic method, using B1 (55.33 mg, 0.25 mmol) instead of A1 gave 5b as a yellow powder (99.57 mg, 93.1%). [α]$_D^{25}$: +24.7 (c=0.36, CHCl$_3$); $^1$H-NMR (300 MHz, CDCl$_3$): δ 8.09 (s, 1H), 7.90 (d, J=8.7 Hz, 1H), 7.69-7.61 (m, 2H), 7.36-7.25 (m, 5H), 7.04 (s, 1H), 5.15-5.13 (m, 1H), 3.44-3.29 (m, 2H); $^{13}$C NMR (300 MHz, CDCl$_3$): δ 175.32, 160.09, 139.05, 137.72, 135.22, 135.18, 129.87, 129.45, 128.83, 127.53, 125.62, 123.85, 122.14, 120.43, 120.37, 119.48, 54.20, 37.26, 29.70; HRMS (ESI): calcd for: C$_{19}$H$_{13}$ClF$_3$NO$_3$S [M−H]$^−$=426.0184, obsd [M−H]$^−$=426.0180.

3-chloro-6-methoxybenzo[b]thiophene-2-carbonyl chloride (5-1)

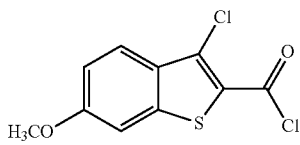 [SMILES: COc1ccc2c(Cl)c(C(=O)Cl)sc2c1]

Following the 5 synthetic method, using p-methoxycinnamic acid (712.72 mg, 4.0 mmol) instead of p-trifluoromethylcinnamic acid gave 5-1 as a yellow crystals; (265.29 mg, 25.4%). $^1$H-NMR (300 MHz, CDCl$_3$): δ 7.89 (d, J=9.0 Hz, 1H), 7.23 (d, J=2.1 Hz, 1H), 7.16 (dd, J=2.1, 9.0 Hz, 1H), 3.95 (s, 3H). $^{13}$C NMR (300 MHz, CDCl$_3$): δ 161.68, 157.82, 142.98, 131.26, 130.96, 126.57, 125.82, 117.76, 103.76, 55.87.

(R)-2-(3-chloro-6-methoxybenzo[b]thiophene-2-carboxamido)-3-phenylpropanoic acid (6a)

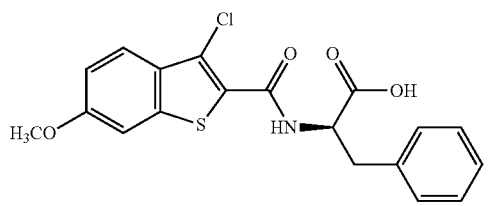 [SMILES: COc1ccc2c(Cl)c(C(=O)N[C@H](Cc3ccccc3)C(=O)O)sc2c1]

Following the 5a synthetic method, using 5-1 instead of 5 gave 6a as a white powder; (92.78 mg, 95.2%). [α]$_D^{25}$: −18.9 (c=0.22, CHCl$_3$); $^1$H-NMR (300 MHz, CDCl$_3$): δ 7.70 (d, J=9.0 Hz, 1H), 7.58 (d, J=6.9 Hz, 1H), 7.34-7.24 (m, 6H), 7.08 (dd, J=2.4, 9.0 Hz, 1H), 5.16-5.13 (m, 1H), 3.90 (s, 3H), 3.43-3.28 (m, 2H); $^{13}$C NMR (300 MHz, CDCl$_3$): δ 175.46, 160.92, 159.95, 140.09, 135.34, 132.52, 130.84, 129.50, 128.99, 128.76, 124.43, 124.14, 119.85, 116.46, 114.00, 104.32, 55.71, 54.04, 37.35; HRMS (ESI): calcd for: C$_{19}$H$_{16}$ClNO$_4$S [M−H]$^−$=388.0416, obsd [M−H]$^−$=388.0407.

(S)-2-(3-chloro-6-methoxybenzo[b]thiophene-2-carboxamido)-3-phenylpropanoic acid (6b)

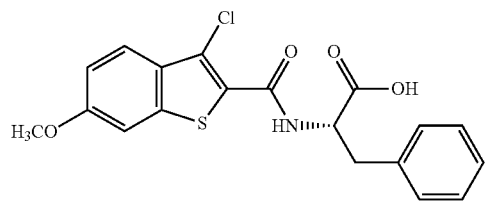 [SMILES: COc1ccc2c(Cl)c(C(=O)N[C@@H](Cc3ccccc3)C(=O)O)sc2c1]

Following the 6a synthetic method, using B1 (55.33 mg, 0.25 mmol) instead of A1 gave 6b as a white powder; (88.78 mg, 91.1%). [α]$_D^{25}$: +16.5 (c=0.29, CHCl$_3$); $^1$H-NMR (300 MHz, CDCl$_3$): δ 8.79 (s, 1H), 7.68 (d, J=9.0 Hz, 1H), 7.59 (d, J=7.2 Hz, 1H), 7.34-7.23 (m, 6H), 7.07 (dd, J=2.4, 9.0 Hz, 1H), 5.18-5.12 (m, 1H), 3.89 (s, 3H), 3.43-3.28 (m, 2H); $^{13}$C NMR (300 MHz, CDCl$_3$): δ 175.50, 160.91, 159.94, 140.08, 135.36, 132.54, 130.83, 129.51, 128.97, 128.76, 127.41, 124.12, 119.87, 116.45, 113.99, 104.31, 55.71, 54.06, 37.36; HRMS (ESI): calcd for: C$_{19}$H$_{16}$ClNO$_4$S [M−H]$^−$=388.0416, obsd [M−H]$^−$=388.0402.

(R)-2-(3-chloro-6-fluorobenzo[b]thiophene-2-carboxamido)-3-(4-hydroxyphenyl)propanoic acid (7a)

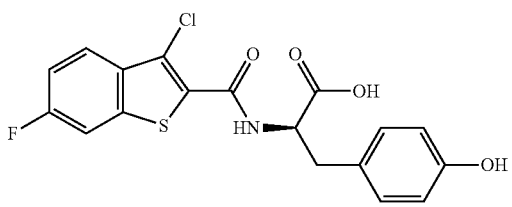 [SMILES: O=C(N[C@H](Cc1ccc(O)cc1)C(=O)O)c1sc2cc(F)ccc2c1Cl]

Following the 9a synthetic method, using 3-chloro-6-fluorobenzo[b]thiophene-2-carbonyl chloride (249.09 mg, 1.0 mmol) instead of 3 gave 7a as a colorless oil; (145.32 mg, 36.9%). [α]$_D^{25}$: +18.3 (c=0.37, CHCl$_3$); $^1$H-NMR (300 MHz, acetone-d$_6$): δ 7.97-7.87 (m, 2H), 7.73 (d, J=6.6 Hz, 1H), 7.45-7.38 (m, 1H), 7.18-7.15 (m, 2H), 6.80-6.77 (m, 2H), 4.96-4.90 (m, 1H), 3.34-3.16 (m, 2H); $^{13}$C NMR (300 MHz, acetone-d$_6$): δ 171.56, 163.89, 160.62, 159.45, 156.42, 139.16, 133.55, 130.54, 127.03, 124.94, 118.51, 115.22, 114.80, 109.29, 108.95, 54.14, 35.98; HRMS (ESI): calcd for: C$_{18}$H$_{13}$ClFNO$_4$S [M−H]$^−$=392.0165, obsd [M−H]$^−$=392.0174.

(S)-2-(3-chloro-6-fluorobenzo[b]thiophene-2-carboxamido)-3-(4-hydroxyphenyl)propanoic acid (7b)

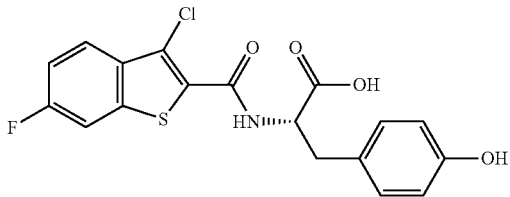 [SMILES: O=C(N[C@@H](Cc1ccc(O)cc1)C(=O)O)c1sc2cc(F)ccc2c1Cl]

Following the 9a synthetic method, using B2 instead of A2 gave 7b as a colorless oil; (147.68 mg, 37.5%). $[\alpha]_D^{25}$: −20.3 (c=0.28, CHCl$_3$); $^1$H-NMR (300 MHz, acetone-d$_6$): δ 7.96-7.87 (m, 2H), 7.75 (d, J=6.0 Hz, 1H), 7.44-7.38 (m, 1H), 7.18-7.15 (m, 2H), 6.79-6.77 (m, 2H), 4.93-4.91 (m, 1H), 3.34-3.17 (m, 2H); $^{13}$C NMR (300 MHz, acetone-d$_6$): δ 171.90, 163.86, 160.58, 159.44, 156.40, 139.13, 133.52, 132.97, 130.55, 127.12, 124.90, 118.49, 115.21, 114.76, 109.26, 108.91, 54.42, 36.03; HRMS (ESI): calcd for: C$_{18}$H$_{13}$ClFNO$_4$S [M−H]$^−$=392.0165, obsd [M−H]$^−$=392.0170.

3-chloro-5,6-difluorobenzo[b]thiophene-2-carbonyl chloride (5-2)

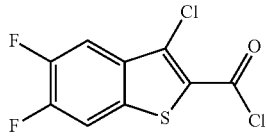 [SMILES: O=C(Cl)c1sc2cc(F)c(F)cc2c1Cl]

Following 5 synthetic method, using 3.4-difluorocinnamic acid (736.56 mg, 4.0 mmol) instead of p-trifluoromethylcinnamic acid gave 5-2 as a yellow crystals; (272.42 mg, 25.5%). $^1$H-NMR (300 MHz, CDCl$_3$): δ 7.83-7.77 (m, 1H), 7.70-7.65 (m, 1H). $^{13}$C NMR (300 MHz, CDCl$_3$): δ 157.62, 154.54, 152.40, 151.11, 149.05, 135.99, 133.59, 112.22, 110.97.

(R)-2-(3-chloro-5,6-difluorobenzo[b]thiophene-2-carboxamido)-3-phenylpropanoic acid (8a)

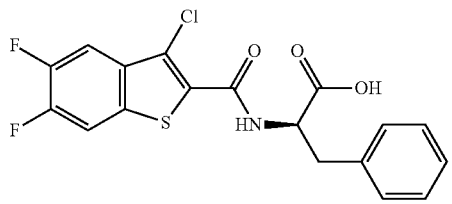 [SMILES: O=C(N[C@H](Cc1ccccc1)C(=O)O)c1sc2cc(F)c(F)cc2c1Cl]

Following the 5a synthetic method, using 5-2 (66.77 mg, 0.25 mmol) instead of 5 gave 8a as a white powder; (91.63 mg, 92.6%). $[\alpha]_D^{25}$: −15.9 (c=0.19, CHCl$_3$); $^1$H-NMR (300 MHz, acetone-d$_6$): δ 7.91 (s, 1H), 7.63-7.52 (m, 3H), 7.37-7.25 (m, 5H), 5.16-5.09 (m, 1H), 3.43-3.28 (m, 2H); $^{13}$C NMR (300 MHz, acetone-d$_6$): δ 175.39, 160.02, 152.99, 151.92, 149.63, 148.61, 135.17, 133.75, 133.25, 129.45, 128.82, 127.53, 118.84, 110.98, 110.77, 110.50, 54.05, 37.28; HRMS (ESI): calcd for: C$_{18}$H$_{12}$ClF$_2$NO$_3$S [M−H]$^−$=394.0122, obsd [M−H]$^−$=394.0137.

(S)-2-(3-chloro-5,6-difluorobenzo[b]thiophene-2-carboxamido)-3-phenylpropanoic acid (8b)

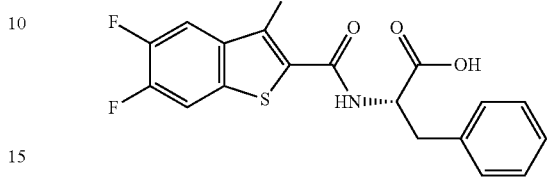

Following the 8a synthetic method, using B1 (55.33 mg, 0.25 mmol) instead of A1 gave 8b as a white powder; (93.51 mg, 94.5%). $[\alpha]_D^{25}$: +22.3 (c=0.43, CHCl$_3$); $^1$H-NMR (300 MHz, acetone-d$_6$): δ 7.80 (s, 1H), 7.64-7.51 (m, 3H), 7.34-7.24 (m, 5H), 5.16-5.10 (m, 1H), 3.43-3.28 (m, 2H); $^{13}$C NMR (300 MHz, acetone-d$_6$): δ 175.44, 160.03, 153.01, 151.93, 149.64, 148.62, 135.14, 133.75, 133.28, 129.45, 128.83, 127.55, 188.89, 110.98, 110.79, 110.53, 54.04, 37.28; HRMS (ESI): calcd for: C$_{18}$H$_{12}$ClF$_2$NO$_3$S [M−H]$^−$=394.0122, obsd [M−H]$^−$=394.0127.

Ethyl 5-fluorobenzo[b]thiophene-2-carboxylate (8)

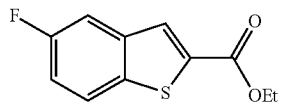 [SMILES: CCOC(=O)c1cc2cc(F)ccc2s1]

To a mixture of 2,5-difluorobenzaldehyde (217.28 μL, 2 mmol) and potassium carbonate (595.53 mg, 2.5 mmol) in DMF (3 mL) was added ethyl thioglycolate (219.30 μL, 2 mmol) dropwise with ice cooling.[7] The mixture was stirred at room temperature for 30 min and at 60° C. for 12 h, poured into water, and extracted with EtOAc. The extract was washed with water, dried, and concentrated, and the residue was suspended in EtOH and collected by filtration gave 8 as crystals; (271.34 mg, 60.5%). $^1$H-NMR (300 MHz, CDCl$_3$): δ 8.00 (s, 1H), 7.83-7.78 (m, 1H), 7.55-7.51 (m, 1H), 7.26-7.19 (m, 1H), 4.46-4.39 (q, 2H), 1.46-1.41 (t, 3H). $^{13}$C NMR (300 MHz, CDCl$_3$): δ 162.47, 159.25, 139.63, 137.60, 136.29, 129.75, 124.11, 116.24, 110.65, 61.74, 14.29.

5-fluorobenzo[b]thiophene-2-carboxylic acid (8-acid)

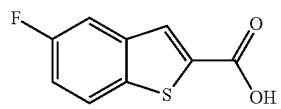 [SMILES: O=C(O)c1cc2cc(F)ccc2s1]

To a mixture of 8 (246.68 mg, 1.1 mmol) and LiOH (75.9 mg, 3.3 mmol) in THF (9 mL) was added MeOH (1 mL) and H$_2$O (3 mL), stirred at room temperature for 6 h. Then HCl (1 M) was added to the reaction mixture to pH=4, and extracted with EtOAc (3×15 mL), wash with H$_2$O (3×20 mL). The organic extracts were dried with Na$_2$SO$_4$ and concentrated under reduced pressure. Purified by flash chromatography on silica gel, using ethyl acetate/hexane (4:1) as eluent, give 8-acid as white powder; (212.79 mg, 98.6%). $^1$H-NMR (300 MHz, acetone-$d_6$): δ 8.14 (s, 1H), 8.10-8.05 (m, 1H), 7.80-7.76 (m, 1H), 7.41-7.34 (m, 1H). $^{13}$C NMR (300 MHz, acetone-$d_6$): δ 162.52, 159.31, 140.12, 137.78, 130.11, 124.65, 116.10, 110.66.

(R)-2-(5-fluorobenzo[b]thiophene-2-carboxamido)-3-phenylpropanoic acid (10a)

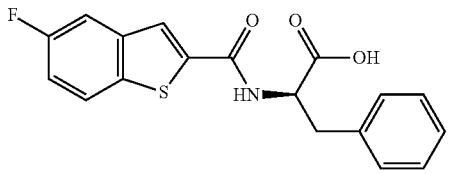 [SMILES: O=C(N[C@H](Cc1ccccc1)C(=O)O)c1cc2cc(F)ccc2s1]

Following the 2a synthetic method, using 8-1 (88.10 mg, 0.5 mmol) instead of 3-chloro-6-methylbenzo[b]thiophene-2-carboxylic acid gave 10a as a colorless oil; (158.29 mg, 92.2%). $[α]_D^{25}$: −16.6 (c=0.31, CHCl$_3$); $^1$H-NMR (300 MHz, CDCl$_3$): δ 7.95 (s, 1H), 7.72-7.67 (m, 1H), 7.60 (s, 1H), 7.38-7.15 (m, 7H), 6.84 (d, J=7.2 Hz, 1H), 5.08-5.06 (m, 1H), 3.38-3.21 (m, 2H); $^{13}$C NMR (300 MHz, acetone-$d_6$): δ 172.07, 162.46, 161.42, 159.27, 141.99, 140.50, 137.50, 136.64, 129.21, 128.33, 126.61, 124.55, 115.22, 114.89, 110.23, 109.92, 54.13, 36.98; HRMS (ESI): calcd for: $C_{18}H_{14}FNO_3S$ [M−H]$^-$=342.0606, obsd [M−H]$^-$=342.0592.

(S)-2-(5-fluorobenzo[b]thiophene-2-carboxamido)-3-phenylpropanoic acid (10b)

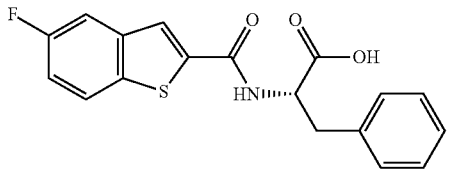 [SMILES: O=C(N[C@@H](Cc1ccccc1)C(=O)O)c1cc2cc(F)ccc2s1]

Following the 10a synthetic method, using B1 (110.65 mg, 0.5 mmol) instead of A1 gave 10b as a white powder; (163.96 mg, 95.5%). $[α]_D^{25}$: +21.8 (c=0.35, CHCl$_3$); $^1$H-NMR (300 MHz, CDCl$_3$): δ 7.97 (s, 1H), 7.74-7.69 (m, 1H), 7.60 (s, 1H), 7.39-7.16 (m, 7H), 6.86 (d, J=7.5 Hz, 1H), 5.09-5.07 (m, 1H), 3.39-3.22 (m, 2H); $^{13}$C NMR (300 MHz, CDCl$_3$): δ 175.03, 162.49, 162.17, 159.27, 139.84, 139.51, 136.42, 135.52, 129.37, 128.76, 127.36, 125.57, 124.05, 115.93, 110.45, 53.87, 37.31; HRMS (ESI): calcd for: $C_{18}H_{14}FNO_3S$ [M−H]$^-$=342.0606, obsd [M−H]$^-$=342.0596.

(R)-2-(3-chlorobenzo[b]thiophene-2-carboxamido)-3-phenylpropanoic acid (11a)

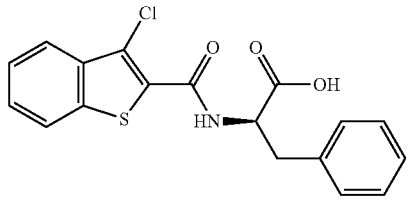 [SMILES: O=C(N[C@H](Cc1ccccc1)C(=O)O)c1sc2ccccc2c1Cl]

Following the 2a synthetic method, using 3-chlorobenzo[b]thiophene-2-carboxylic acid (106.33 mg, 0.5 mmol) instead of 3-chloro-6-methylbenzo[b]thiophene-2-carboxylic acid gave 1a as a colorless oil; (167.14 mg, 92.9%). $[α]_D^{25}$: −19.9 (c=0.34, CHCl$_3$); $^1$H-NMR (300 MHz, acetone-$d_6$): δ 8.05-7.99 (m, 1H), 7.90-7.87 (m, 1H), 7.81 (d, J=8.1 Hz, 1H), 7.61-7.54 (m, 2H), 7.37-7.22 (m, 5H), 5.05-4.98 (m, 1H), 3.45-3.27 (m, 2H); $^{13}$C NMR (300 MHz, acetone-$d_6$): δ 171.54, 159.75, 137.75, 136.74, 136.67, 132.78, 129.51, 128.40, 127.67, 126.88, 125.74, 123.03, 122.82, 118.87, 54.10, 36.83; HRMS (ESI): calcd for: $C_{18}H_{14}ClNO_3S$ [M−H]$^-$=358.0310, obsd [M−H]$^-$=358.0318.

(S)-2-(3-chlorobenzo[b]thiophene-2-carboxamido)-3-phenylpropanoic acid (11b)

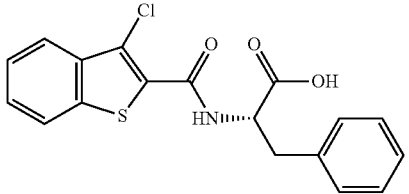 [SMILES: O=C(N[C@@H](Cc1ccccc1)C(=O)O)c1sc2ccccc2c1Cl]

Following the 11a synthetic method, using B1 (110.65 mg, 0.5 mmol) instead of A1 gave 11b as a colorless oil; (164.98 mg, 91.7%). $[α]_D^{25}$: +23.3 (c=0.42, CHCl$_3$); $^1$H-NMR (300 MHz, acetone-$d_6$): δ 8.06-8.00 (m, 1H), 7.91-7.87 (m, 1H), 7.80 (d, J=6.9 Hz, 1H), 7.62-7.55 (m, 2H), 7.37-7.22 (m, 5H), 5.05-4.98 (m, 1H), 3.45-3.26 (m, 2H); $^{13}$C NMR (300 MHz, acetone-$d_6$): δ 171.56, 159.74, 137.75, 136.74, 136.67, 132.78, 129.51, 128.40, 127.67, 126.88, 125.74, 123.03, 122.83, 118.86, 54.09, 36.83; HRMS (ESI): calcd for: $C_{18}H_{14}ClNO_3S$ [M−H]$^-$=358.0310, obsd [M−H]$^-$=358.0312.

3-chloro-5-fluorobenzo[b]thiophene-2-carbonyl chloride (5-3)

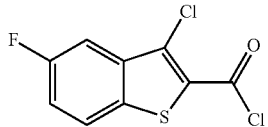 [SMILES: O=C(Cl)c1sc2ccc(F)cc2c1Cl]

Following 5 synthetic method, using 3-fluorocinnamic acid (664.60 mg, 4.0 mmol) instead of p-trifluoromethylcinnamic acid gave 3-chloro-5-fluorobenzo[b]thiophene-2-carbonyl chloride as a yellow crystals; (279.97 mg, 28.1%). $^1$H-NMR (300 MHz, CDCl$_3$): δ 7.87-7.82 (m, 1H), 7.71-7.67 (m, 1H), 7.45-7.38 (m, 1H). $^{13}$C NMR (300 MHz, CDCl$_3$): δ 163.12, 159.84, 158.09, 135.88, 131.76, 124.71, 119.67, 119.33, 110.13.

(R)-2-(3-chloro-5-fluorobenzo[b]thiophene-2-carboxamido)-3-phenylpropanoic acid (12a)

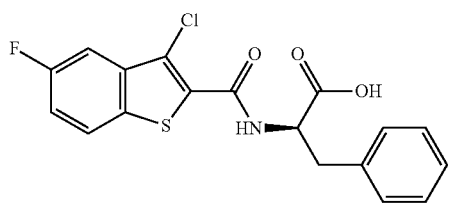 [SMILES: O=C(N[C@H](Cc1ccccc1)C(=O)O)c1sc2ccc(F)cc2c1Cl]

Following the 5a synthetic method, using 3-chloro-5-fluorobenzo[b]thiophene-2-carbonyl chloride (62.27 mg, 0.25 mmol) instead of 5 gave 12a as a white powder; (82.6 mg, 91.7%). $[\alpha]_D^{25}$: −16.8 (c=0.16, CHCl$_3$); $^1$H-NMR (300 MHz, acetone-d$_6$): δ 8.10-8.06 (m, 1H), 7.81 (d, J=6.9, 1H), 7.61-7.57 (m, 1H), 7.46-7.28 (m, 6H), 5.03-4.97 (m, 1H), 3.45-3.26 (m, 2H); $^{13}$C NMR (300 MHz, acetone-d$_6$): δ 171.51, 163.02, 159.79, 138.08, 136.67, 135.36, 133.43, 129.49, 128.39, 126.88, 125.28, 118.22, 116.80, 116.46, 108.25, 107.92, 54.15, 36.79; HRMS (ESI): calcd for: C$_{18}$H$_{13}$ClFNO$_3$S [M−H]$^−$=376.0216, obsd [M−H]$^−$=376.0200.

(S)-2-(3-chloro-5-fluorobenzo[b]thiophene-2-carboxamido)-3-phenylpropanoic acid (12b)

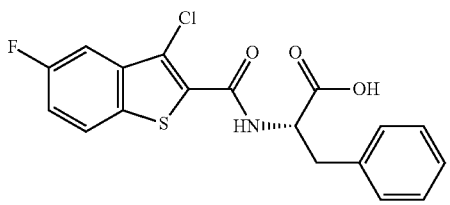 [SMILES: O=C(N[C@@H](Cc1ccccc1)C(=O)O)c1sc2ccc(F)cc2c1Cl]

Following the 12a synthetic method, using B1 (55.33 mg, 0.25 mmol) instead of A1 gave 12b as a white powder; (87.65 mg, 92.8%). $[\alpha]_D^{25}$: +22.3 (c=0.29, CHCl$_3$); $^1$H-NMR (300 MHz, acetone-d$_6$): δ 8.11-8.06 (m, 1H), 7.81 (d, J=7.2, 1H), 7.61-7.57 (m, 1H), 7.46-7.22 (m, 6H), 5.03-4.97 (m, 1H), 3.40-3.26 (m, 2H); $^{13}$C NMR (300 MHz, acetone-d$_6$): δ 171.50, 163.02, 159.80, 138.09, 136.66, 135.36, 133.46, 129.49, 128.39, 126.88, 125.29, 118.28, 116.80, 116.46, 108.25, 107.93, 54.14, 36.79; HRMS (ESI): calcd for: C$_{18}$H$_{13}$ClFNO$_3$S [M−H]$^−$=376.0216, obsd [M−H]$^−$=376.0221.

Ethyl 6-fluorobenzo[b]thiophene-2-carboxylate (8-1)

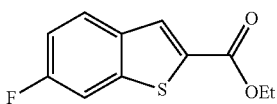 [SMILES: CCOC(=O)c1cc2ccc(F)cc2s1]

Following 8 synthetic method, using 2,4-difluorobenzaldehyde (218.8 μL, 2 mmol) instead of 2,5-difluorobenzaldehyde gave 8-1 as a white crystals; (278.97 mg, 62.2%). $^1$H-NMR (300 MHz, CDCl$_3$): δ 8.02 (s, 1H), 7.86-7.81 (m, 1H), 7.56-7.52 (m, 1H), 7.21-7.14 (m, 1H), 4.45-4.38 (q, 2H), 1.45-1.40 (t, 3H). $^{13}$C NMR (300 MHz, CDCl$_3$): δ 163.60, 160.31, 143.37, 135.28, 133.75, 129.82, 126.89, 114.57, 108.83, 61.65, 14.31.

6-fluorobenzo[b]thiophene-2-carboxylic acid (8-1-acid)

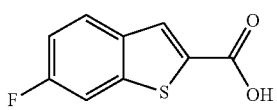

Following the 5-fluorobenzo[b]thiophene-2-carboxylic acid synthetic method gave 8-1-acid as a white powder; (211.72 mg, 98.1%). $^1$H-NMR (300 MHz, acetone-d$_6$): δ 8.14 (s, 1H), 8.08-8.04 (m, 1H), 7.86-7.82 (m, 1H), 7.34-7.27 (m, 1H). $^{13}$C NMR (300 MHz, acetone-d$_6$): δ 163.56, 160.31, 143.43, 135.86, 130.06, 127.34, 114.39, 108.81.

(R)-2-(6-fluorobenzo[b]thiophene-2-carboxamido)-3-phenylpropanoic acid (13a)

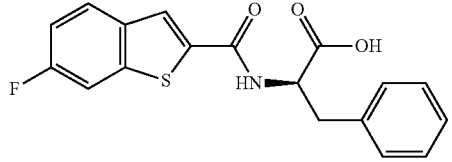 [SMILES: O=C(N[C@H](Cc1ccccc1)C(=O)O)c1cc2ccc(F)cc2s1]

Following the 2a synthetic method, using 8-1-acid (98.10 mg, 0.5 mmol) instead of 3-chloro-6-methylbenzo[b]thiophene-2-carboxylic acid gave 13a as a colorless oil (159.84 mg, 93.1%). $[\alpha]_D^{25}$: −21.1 (c=0.33, CHCl$_3$); $^1$H-NMR (300 MHz, acetone-d$_6$): δ 8.03 (d, J=8.1 Hz, 1H), 7.98 (s, 1H), 7.90-7.86 (m, 1H), 7.75-7.71 (m, 1H), 7.34-7.13 (m, 6H), 4.95-4.87 (m, 1H), 3.36-3.10 (m, 2H); $^{13}$C NMR (300 MHz, acetone-d$_6$): δ 172.09, 163.11, 161.49, 159.87, 142.28, 139.46, 137.49, 136.19, 129.22, 128.33, 126.89, 126.63, 126.61, 124.44, 114.09, 108.67, 54.08, 37.01; HRMS (ESI): calcd for: C$_{18}$H$_{14}$FNO$_3$S [M−H]$^−$=342.0606, obsd [M−H]$^−$=342.0594.

(S)-2-(6-fluorobenzo[b]thiophene-2-carboxamido)-3-phenylpropanoic acid (13b)

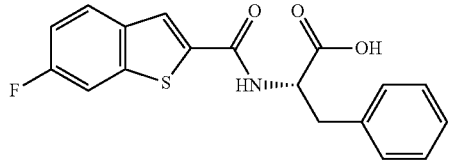 [SMILES: O=C(N[C@@H](Cc1ccccc1)C(=O)O)c1cc2ccc(F)cc2s1]

Following the 13a synthetic method, using B1 (110.65 mg, 0.5 mmol) instead of A1 gave 13b as colorless oil; (154.68 mg, 90.1%). $[\alpha]_D^{25}$: +15.7 (c=0.26, CHCl$_3$); $^1$H-NMR (300 MHz, acetone-d$_6$): δ 8.08 (d, J=8.1 Hz, 1H), 8.03 (s, 1H), 7.96-7.91 (m, 1H), 7.80-7.76 (m, 1H), 7.39-7.18 (m, 6H), 4.98-4.92 (m, 1H), 3.36-3.15 (m, 2H); $^{13}$C NMR (300 MHz, acetone-d$_6$): δ 172.17, 163.11, 161.48, 159.86, 142.28, 139.43, 137.51, 136.19, 129.23, 128.32, 126.89, 126.76, 126.60, 124.43, 114.09, 108.67, 54.12, 37.02; HRMS (ESI): calcd for: C$_{18}$H$_{14}$FNO$_3$S [M−H]$^−$=342.0606, obsd [M−H]$^−$=342.0593.

(R)-2-(2-fluorophenylsulfonamido)-3-phenylpropanoic acid (14a)

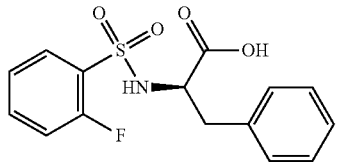 [SMILES: O=C(O)[C@@H](Cc1ccccc1)NS(=O)(=O)c1ccccc1F]

To a solution of A1 (110.65 mg, 0.5 mmol) in dry dichloromethane (3 mL) at 0° C. was added triethylamine (0.086 mL, 0.55 mmol) and 2-fluorobenzenesulfonyl chloride (66.88 µL, 0.50 mmol). The reaction mixture was stirred at room temperature overnight and concentrated under reduced pressure. Then dissolved the oil mixture in 2 mL CH$_2$Cl$_2$ and 2 mL TFA was add under argon. The reaction mixture was stirred at room temperature for 12 h (TLC monitor). The solvent was removed under reduce pressure and the crude compound was purified by flash chromatography on silica gel, using ethyl acetate/hexane (2:5) as the eluent, gave 14a; (105.42 mg, 65.2%). [α]$_D^{25}$: −11.7 (c=0.24, CHCl$_3$); $^1$H-NMR (300 MHz, CDCl$_3$): δ 7.82 (dd, J=1.8, 7.8 Hz, 1H), 7.60-7.52 (m, 1H), 7.27-7.21 (m, 4H), 7.16-7.09 (m, 3H), 5.27 (d, J=9 Hz, 1H), 4.41 (m, 1H), 3.20-3.06 (m, 2H); $^{13}$C NMR (300 MHz, acetone-d$_6$): δ 171.41, 160.51, 157.15, 136.54, 134.91, 134.80, 129.48, 129.31, 128.18, 126.68, 124.15, 117.04, 116.76, 57.31, 38.36; HRMS (ESI): calcd for: C$_{15}$H$_{14}$FNO$_4$S [M+H]$^+$=324.0690, obsd [M+H]$^+$= 324.0700.

(S)-2-(2-fluorophenylsulfonamido)-3-phenylpropanoic acid (14b)

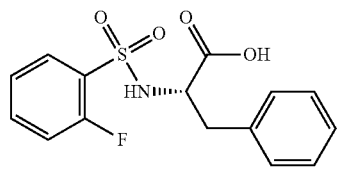 [SMILES: O=C(O)[C@H](Cc1ccccc1)NS(=O)(=O)c1ccccc1F]

Following the 14a synthetic method, using B1 (110.65 mg, 0.5 mmol) instead of A1 gave 14b as a colorless oil; (102.01 mg, 63.1%). [α]$_D^{25}$: +16.3 (c=0.39, CHCl$_3$); $^1$H-NMR (300 MHz, CDCl$_3$): δ 7.82 (dd, J=1.8, 7.8 Hz, 1H), 7.59-7.52 (m, 1H), 7.26-7.21 (m, 4H), 7.15-7.08 (m, 3H), 5.27 (d, J=9 Hz, 1H), 4.43 (m, 1H), 3.20-3.05 (m, 2H); $^{13}$C NMR (300 MHz, acetone-d$_6$): δ 171.53, 160.51, 157.15, 136.55, 134.91, 134.79, 129.48, 129.31, 128.18, 126.68, 124.15, 117.04, 116.75, 57.32, 38.37; HRMS (ESI): calcd for C$_{15}$H$_{14}$FNO$_4$S: [M+Na]$^+$=346.0508, obsd [M+Na]$^+$=324.0520.

(R)-2-(3-fluorophenylsulfonamido)-3-phenylpropanoic acid (15a)

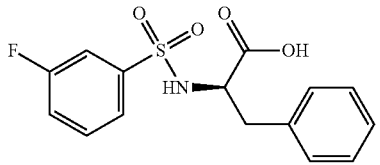 [SMILES: O=C(O)[C@@H](Cc1ccccc1)NS(=O)(=O)c1cccc(F)c1]

Following the 14a synthetic method, using 3-fluorobenzenesulfonyl chloride (66.19 µL, 0.5 mmol) instead of 2-fluorobenzenesulfonyl chloride gave 15a as a colorless oil; (103.95 mg, 64.3%). [α]$_D^{25}$: −16.5 (c=0.31, CHCl$_3$); $^1$H-NMR (300 MHz, CDCl$_3$): δ 7.49-7.32 (m, 3H), 7.25-7.20 (m, 4H), 7.10-7.08 (m, 2H), 5.45 (d, J=7.8 Hz, 1H), 4.25 (m, 1H), 3.19-2.91 (m, 2H); $^{13}$C NMR (300 MHz, CDCl$_3$): δ 163.89, 160.56, 141.51, 134.71, 130.88, 129.34, 128.68, 127.47, 122.75, 120.24, 119.96, 114.49, 114.17, 56.86 38.74; HRMS (ESI): calcd for: C$_{15}$H$_{14}$FNO$_4$S [M−H]$^−$=322.0555, obsd [M−H]$^−$=322.0549.

(S)-2-(3-fluorophenylsulfonamido)-3-phenylpropanoic acid (15b)

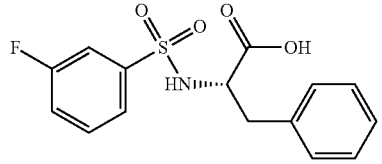 [SMILES: O=C(O)[C@H](Cc1ccccc1)NS(=O)(=O)c1cccc(F)c1]

Following the 15a synthetic method, using B1 (110.65 mg, 0.5 mmol) instead of A1 gave 14b as a colorless oil; (106.54 mg, 65.9%). [α]$_D^{25}$: +15.1 (c=0.28, CHCl$_3$); $^1$H-NMR (300 MHz, CDCl$_3$): δ 7.53-7.50 (m, 1H), 7.40-7.36 (m, 2H), 7.27-7.22 (m, 4H), 7.12-7.08 (m, 2H), 5.11 (d, J=9 Hz, 1H), 4.26 (m, 1H), 3.20-2.98 (m, 2H); $^{13}$C NMR (300 MHz, CDCl$_3$): δ 163.89, 160.56, 141.49, 134.67, 130.88, 129.33, 128.70, 127.49, 122.75, 120.26, 119.98, 114.49, 114.17, 56.85, 38.72; HRMS (ESI): calcd for: C$_{15}$H$_{14}$FNO$_4$S [M−H]$^−$= 322.0555, obsd [M−H]$^−$=322.0543.

(R)-2-(4-fluorophenylsulfonamido)-3-phenylpropanoic acid (16a)

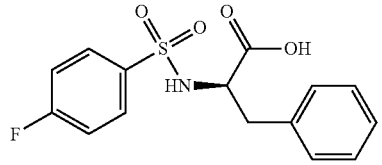 [SMILES: O=C(O)[C@@H](Cc1ccccc1)NS(=O)(=O)c1ccc(F)cc1]

Following the 14a synthetic method, using 4-fluorobenzenesulfonyl chloride (97.31 mg, 0.5 mmol) instead of 2-fluorobenzenesulfonyl chloride gave 16a as a colorless oil; (108.48 mg, 67.1%). [α]$_D^{25}$: −19.1 (c=0.41, CHCl$_3$); $^1$H-NMR (300 MHz, CDCl$_3$): δ 7.77-7.73 (m, 2H), 7.24-7.21 (m, 7H), 6.92 (d, J=9 Hz, 1H), 4.21-4.14 (m, 1H), 3.15-2.90 (m, 2H); $^{13}$C NMR (300 MHz, acetone-d$_6$): δ 171.55, 166.28, 162.95, 137.53, 136.53, 129.74, 129.62, 129.39, 128.24, 126.68, 115.93, 115.63, 57.29, 38.49; HRMS (ESI): calcd for: C$_{15}$H$_{14}$FNO$_4$S [M+Na]$^+$=346.0520, obsd [M+Na]$^+$= 346.0513.

(S)-2-(4-fluorophenylsulfonamido)-3-phenylpropanoic acid (16b)

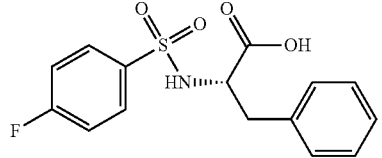 [SMILES: O=C(O)[C@H](Cc1ccccc1)NS(=O)(=O)c1ccc(F)cc1]

Following the 16a synthetic method, using B1 (110.65 mg, 0.5 mmol) instead of A1 gave 16b as a colorless oil (102.34 mg, 63.3%). [α]$_D^{25}$: +14.4 (c=0.34, CHCl$_3$); $^1$H-NMR (300 MHz, CDCl$_3$): δ 7.78-7.71 (m, 2H), 7.26-7.17 (m, 7H), 6.92 (d, J=9 Hz, 1H), 4.25-4.13 (m, 1H), 3.15-2.90 (m, 2H); $^{13}$C NMR (300 MHz, acetone-d$_6$): δ 171.56, 166.28, 162.95, 137.52, 136.53, 129.74, 129.62, 129.39, 128.24, 126.68, 115.94, 115.63, 57.31, 38.48; HRMS (ESI): calcd for: C$_{15}$H$_{14}$FNO$_4$S [M+Na]$^+$=346.0520, obsd [M+Na]$^+$= 346.0523.

(R)-2-(2-fluorophenylsulfonamido)-3-(4-hydroxyphenyl)propanoic acid (17a)

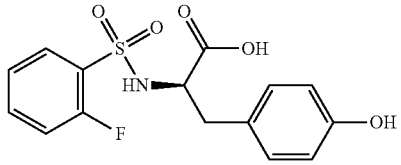 [SMILES: O=C(O)[C@@H](Cc1ccc(O)cc1)NS(=O)(=O)c1ccccc1F]

Following general method B, to a solution of A2 (118.65 mg, 0.5 mmol) in dry dichloromethane (3 mL) at 0° C. was added triethylamine (0.086 mL, 0.55 mmol) and 2-fluorobenzenesulfonyl chloride (147.14 μL, 1.1 mmol). The reaction mixture was stirred at room temperature overnight and then washed with H$_2$O (3×15 mL) and the organic extracts were dried (Na$_2$SO$_4$) and concentrated under reduced pressure. Purified by flash chromatography on silica gel, using ethyl acetate/hexane (2:5) as the eluent, give 10 as a colorless oil (238.87 mg, 86.3%). [α]$_D^{25}$: +31.8 (c=0.29, CHCl$_3$); $^1$H-NMR (300 MHz, CDCl$_3$): δ 7.86-7.75 (m, 2H), 7.73-7.65 (m, 1H), 7.60-7.53 (m, 1H), 7.34-7.22 (m, 3H), 7.19-7.11 (m, 1H), 7.04-6.99 (m, 1H), 5.35 (d, J=8.7 Hz, 1H), 4.19-4.12 (m, 1H), 3.03-3.01 (d, 2H), 1.20 (s, 9H); $^{13}$C NMR (300 MHz, CDCl$_3$): δ 169.17, 161.10, 157.65, 148.42, 136.86, 135.22, 134.74, 131.43, 130.99, 129.95, 127.74, 124.59, 124.34, 123.55, 122.00, 117.57, 117.29, 117.13, 116.84, 83.12, 57.03, 39.06, 27.62.

Intermediate 10 (138.40 mg, 0.25 mmol) was dissolved in a solution of 2 N NaOH/EtOH/water (0.96 g/10 mL/2 mL) and heated at 80° C. After 24 h, the solvent was evaporated and the byproduct was recrystallized from ethanol. The side product (benzenesulfonic acid) was filtered off, and the filtrate was evaporated to dryness.

Then dissolved the oil mixture in 2 mL CH$_2$Cl$_2$ and 2 mL TFA was added under argon. The reaction mixture was stirred at room temperature for 12 h (TLC monitor). The solvent was removed under reduce pressure and the crude compound was purified by flash chromatography on silica gel, using ethyl acetate/hexane (1:5) as the eluent, gave 17a as a colorless oil; (55.16 mg, 60.3%). [α]$_D^{25}$: +17.7 (c=0.32, CHCl$_3$); $^1$H-NMR (300 MHz, acetone-d$_6$): δ 7.75-7.59 (m, 2H), 7.30-7.16 (m, 2H), 7.06-7.03 (m, 2H), 6.92 (s, 1H), 6.69-6.66 (m, 2H), 4.19-4.15 (m, 1H), 3.09-2.87 (m, 2H); $^{13}$C NMR (300 MHz, acetone-d$_6$): δ 171.58, 160.50, 157.14, 156.14, 134.81, 130.31, 129.48, 129.08, 127.02, 124.17, 117.03, 116.75, 114.98, 57.59, 37.61; HRMS (ESI): calcd for: C$_{15}$H$_{14}$FNO$_5$S [M+Na]$^+$=362.0468, obsd [M+Na]$^+$=362.0480.

(S)-2-(2-fluorophenylsulfonamido)-3-(4-hyroxyphenyl)propanoic acid (17b)

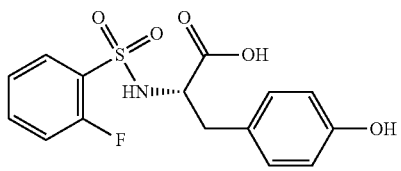 [SMILES: O=C(O)[C@H](Cc1ccc(O)cc1)NS(=O)(=O)c1ccccc1F]

Following 10 synthesis method, using B2 (118.65 mg, 0.5 mmol) instead of A2 gave 17b as colorless oil; (82.42 mg, 48.6%). [α]$^2$: −15.9 (c=0.39, CHCl$_3$); $^1$H-NMR (300 MHz, acetone-d$_6$): δ 7.76-7.70 (m, 1H), 7.64-7.59 (m, 1H), 7.30-7.16 (m, 2H), 7.06-7.05 (m, 2H), 6.69-6.66 (m, 2H), 4.18-4.14 (m, 1H), 3.09-2.87 (m, 2H); $^{13}$C NMR (300 MHz, acetone-d$_6$): δ 171.71, 160.51, 157.14, 156.12, 134.81, 130.35, 129.50, 129.06, 127.08, 124.17, 117.03, 116.75, 114.97, 57.65, 37.63; HRMS (ESI): calcd for: C$_{15}$H$_{14}$FNO$_5$S [M+Na]$^+$=362.0468, obsd [M+Na]$^+$=362.0468.

(R)-2-(3-fluorophenylsulfonamido)-3-(4-hydroxyphenyl)propanoic acid (18a)

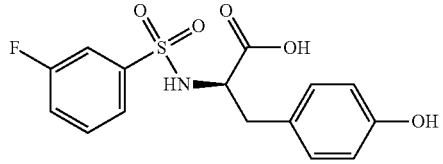 [SMILES: O=C(O)[C@@H](Cc1ccc(O)cc1)NS(=O)(=O)c1cccc(F)c1]

Following 17a synthetic method, using 2-fluorobenzenesulfonyl chloride (145.62 μL, 1.1 mmol) instead of 2-fluorobenzenesulfonyl chloride gave the final compound 18a as a colorless oil; (77.34 mg, 45.6%). [α]$_D^{25}$: +21.3 (c=0.25, CHCl$_3$); $^1$H-NMR (300 MHz, acetone-d$_6$): δ 7.95-7.76 (m, 3H), 7.41-7.25 (m, 6H), 5.04-4.97 (m, 1H), 3.45-2.26 (m, 2H); $^{13}$C NMR (300 MHz, acetone-d$_6$): δ 171.50, 163.90, 160.62, 139.15, 136.64, 133.50, 129.49, 128.40, 126.89, 124.94, 118.56, 115.15, 109.30, 54.04, 36.79; HRMS (ESI): calcd for: C$_{15}$H$_{14}$FNO$_5$S [M+Na]$^+$=362.0469, obsd [M+Na]$^+$=362.0475.

(S)-2-(3-fluorophenylsulfonamido)-3-(4-hydroxyphenyl)propanoic acid (18b)

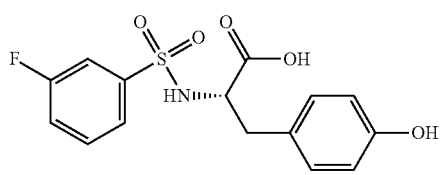 [SMILES: O=C(O)[C@H](Cc1ccc(O)cc1)NS(=O)(=O)c1cccc(F)c1]

Following 18a synthetic method, using B2 (118.65 mg, 0.5 mmol) instead of A2 gave 18b as a colorless oil; (56.33 mg, 49.8%). [α]$_D^{25}$: −14.4 (c=0.27, CHCl$_3$); $^1$H-NMR (300 MHz, acetone-d$_6$): δ 8.20 (s, 1H), 7.56-7.48 (m, 2H), 7.44-7.35 (m, 2H), 7.03-6.95 (m, 3H), 6.70-6.65 (m, 2H), 4.18-4.11 (m, 1H), 3.06-2.81 (m, 2H); $^{13}$C NMR (300 MHz, acetone-d$_6$): δ 171.53, 163.77, 160.48, 156.28, 143.54, 131.00, 130.36, 126.92, 122.75, 119.25, 115.07, 113.89, 113.57, 57.63, 37.74; HRMS (ESI): calcd for: C$_{15}$H$_{14}$FNO$_5$S [M+Na]$^+$= 362.0469, obsd [M+Na]$^+$=362.0485.

(R)-2-(4-fluorophenylsulfonamido)-3-(4-hydroxyphenyl)propanoic acid (19a)

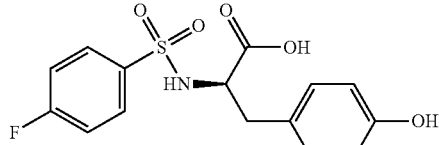

Following 17a synthetic method, using 4-fluorobenzenesulfonyl chloride (214.08 mg, 1.1 mmol) instead of 2-fluorobenzenesulfonyl chloride gave the final compound 19a; as a colorless oil; (93.99 mg, 55.4%). $[\alpha]_D^{25}$: +12.8 (c=0.26, CHCl$_3$); $^1$H-NMR (300 MHz, CDCl$_3$): δ 7.77-7.73 (m, 2H), 7.24-7.21 (m, 7H), 6.92 (d, J=9 Hz, 1H), 4.21-4.14 (m, 1H), 3.15-2.90 (m, 2H); $^{13}$C NMR (300 MHz, acetone-d$_6$): δ 171.55, 166.28, 162.95, 137.53, 136.53, 129.74, 129.62, 129.39, 128.24, 126.68, 115.93, 115.63, 57.29, 38.49; HRMS (ESI): calcd for: C$_{15}$H$_{14}$FNO$_4$S [M+Na]$^+$=346.0520, obsd [M+Na]$^+$=346.0513.

(S)-2-(4-fluorophenylsulfonamido)-3-(4-hydroxyphenyl)propanoic acid (19b)

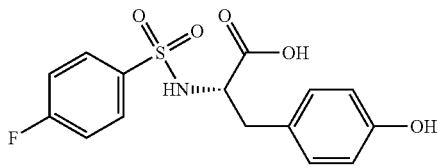 [SMILES: O=C(O)[C@H](Cc1ccc(O)cc1)NS(=O)(=O)c1ccc(F)cc1]

Following 19a synthetic method, using B2 (118.65 mg, 0.5 mmol) instead of A2 gave 19b as a colorless oil; (96.03 mg, 56.6%). $[\alpha]_D^{25}$: -13.7 (c=0.23, CHCl$_3$); $^1$H-NMR (300 MHz, CDCl$_3$): δ 7.78-7.71 (m, 2H), 7.26-7.17 (m, 7H), 6.92 (d, J=9 Hz, 1H), 4.25-4.13 (m, 1H), 3.15-2.90 (m, 2H); $^{13}$C NMR (300 MHz, acetone-d$_6$): δ 171.56, 166.28, 162.95, 137.52, 136.53, 129.74, 129.62, 129.39, 128.24, 126.68, 115.94, 115.63, 57.31, 38.48; HRMS (ESI): calcd for: C$_{15}$H$_{14}$FNO$_4$S [M+Na]$^+$=346.0520, obsd [M+Na]$^+$=346.0523.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:
1. A compound of the formula:

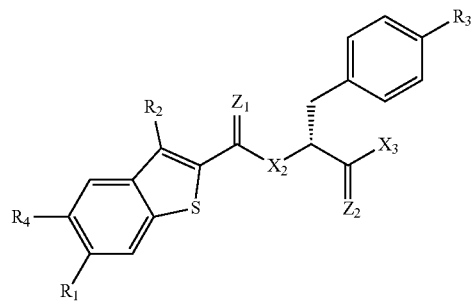

wherein
X$^2$ is independently —NR$^a$—, —O— or —S—;
each of Z$^1$, and Z$^2$ is independently =NR$^a$, =O or =S;
X$^3$ is —NR$^a$R$^b$, —OR$^c$, or —SR$^d$;
each of R$_1$, R$_2$, R$_3$, and R$_4$ is independently hydrogen, alkyl, —OR$^c$, halide, —NR$^a$R$^b$, or —SR$^d$, provided at least one of R$_1$ and R$_4$ is not hydrogen;
each R$^a$ is independently hydrogen, alkyl, or a nitrogen protecting group;
R$^b$ is hydrogen or alkyl;
each R$^c$ is independently hydrogen, alkyl, or a hydroxyl protecting group;
R$^d$ is hydrogen, alkyl, or a thiol protecting group.
2. The compound of claim 1 wherein Z$^1$ and Z$^2$ are O.
3. The compound of claim 1, wherein X$^2$ is NR$^a$.
4. The compound of claim 3, wherein R$^a$ is hydrogen.
5. The compound of claim 1, wherein X$^3$ is OR$^c$.
6. The compound of claim 5, wherein R$^c$ is hydrogen.
7. The compound of claim 1, wherein
R$_1$ is hydrogen, halide, alkyl, haloalkyl, or —OR$^c$;
each of R$_2$ and R$_4$ is independently hydrogen or halide; and
R$_3$ is hydrogen, halide, or —OR$^c$, and wherein R$^e$ is hydrogen, alkyl, or a hydroxyl protecting group,
provided at least one of R$_1$ and R$_4$ is not hydrogen.
8. The compound of claim 7, wherein R$_1$ is hydrogen, methyl, trifluoromethyl, Cl, F, or methoxy.
9. The compound of claim 7, wherein R$_2$ is hydrogen, F, or Cl.
10. The compound of claim 7, wherein R$_3$ is hydrogen, Cl, or OH.
11. The compound of claim 7, wherein R$_4$ is hydrogen or F.
12. A composition comprising a compound of claim 1.
13. A method for inhibiting Toll-like receptor 3 (TLR3)/double-stranded RNA (dsRNA) complex formation comprising contacting a cell with an effective amount of a compound of claim 1.

* * * * *